(12) United States Patent
Wakabayashi et al.

(10) Patent No.: US 8,047,995 B2
(45) Date of Patent: Nov. 1, 2011

(54) ULTRASONIC TRANSDUCER, METHOD OF MANUFACTURING ULTRASONIC TRANSDUCER, ULTRASONIC DIAGNOSTIC APPARATUS, AND ULTRASONIC MICROSCOPE

(75) Inventors: Katsuhiro Wakabayashi, Hachioji (JP); Hideo Adachi, Iruma (JP); Mamoru Hasegawa, Nagano (JP); Kazuya Matsumoto, Nagano (JP); Kazuhisa Karaki, Nagano (JP); Yoshitaka Kamiya, Nagano (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 202 days.

(21) Appl. No.: 12/197,706

(22) Filed: Aug. 25, 2008

(65) Prior Publication Data

US 2009/0058228 A1 Mar. 5, 2009

(30) Foreign Application Priority Data

Aug. 28, 2007 (JP) ................................ 2007-221688
Aug. 28, 2007 (JP) ................................ 2007-221690
Aug. 28, 2007 (JP) ................................ 2007-221691

(51) Int. Cl.
*A61B 8/00* (2006.01)
(52) U.S. Cl. ........................................ 600/459; 310/311
(58) Field of Classification Search .................. 310/334, 310/335, 336, 337, 330, 311, 348, 344; 367/157, 367/163, 181; 600/437, 459; *H01L 41/08, H01L 41/09; H04R 19/00*
See application file for complete search history.

(56) References Cited

U.S. PATENT DOCUMENTS

| 7,940,603 | B2 * | 5/2011 | Adachi et al. ................. 367/181 |
| 2002/0135272 | A1 | 9/2002 | Toda |
| 2007/0057603 | A1 | 3/2007 | Azuma et al. |
| 2007/0161896 | A1 * | 7/2007 | Adachi et al. ................. 600/437 |
| 2009/0058228 | A1 * | 3/2009 | Wakabayashi et al. ....... 310/334 |

FOREIGN PATENT DOCUMENTS

| DE | 89 10 743 U1 | 12/1989 |
| JP | 02-052599 | 2/1990 |
| JP | 2005-506783 | 3/2005 |
| JP | 2005-510264 | 4/2005 |
| JP | 2006-050314 | 2/2006 |
| JP | 2006-157777 | 6/2006 |
| JP | 2006-287279 | 10/2006 |
| WO | WO 03/035281 A2 | 5/2003 |

OTHER PUBLICATIONS

Voorthuyzen J.A. et al., "Semiconductor-Based Electret Sensors for Sound and Pressure", *IEEE Transactions on Electrical Insulation* 24(2):267-276, XP-009110431 (1989).
English-language abstract only of International Publication No. WO 03/011749 A2 dated Feb. 13, 2003.
English-language abstract only of International Publication No. WO 03/035281 A2 dated May 1, 2003.

* cited by examiner

*Primary Examiner* — Walter Benson
*Assistant Examiner* — Karen B Addison
(74) *Attorney, Agent, or Firm* — Scully, Scott, Murphy & Presser, P.C.

(57) ABSTRACT

A ultrasonic transducer of the invention comprises: a transducer cell including a first electrode and a second electrode disposed separated from the first electrode by an air gap portion; and an electret for applying a potential difference between the first electrode and the second electrode. The electret is disposed in a region where at least a part thereof does not overlap with the transducer cell when viewed from a transmitting direction of ultrasonic waves.

15 Claims, 25 Drawing Sheets

ULTRASONIC TRANSDUCER, METHOD OF MANUFACTURING ULTRASONIC TRANSDUCER, ULTRASONIC DIAGNOSTIC APPARATUS, AND ULTRASONIC MICROSCOPE

CROSS REFERENCE TO RELATED ART

This application claims benefit of Japanese Applications No. 2007-221688 filed on Aug. 28, 2007, No. 2007-221690 filed on Aug. 28, 2007 and No. 2007-221691 filed on Aug. 28, 2007, the contents of which are incorporated herein by their reference.

BACKGROUND OF THE INVENTION

1. Field of the Invention

The present invention relates to a capacitive ultrasonic transducer including an electret, a method of manufacturing the ultrasonic transducer, an ultrasonic diagnostic apparatus, and an ultrasonic microscope.

2. Description of Related Art

Ultrasonic diagnostics, which is performed by irradiating ultrasonic waves to a subject to make a diagnosis on a condition of the subject based on an echo signal from the subject, has been in common use. One of the examples of ultrasonic diagnostic apparatuses used in this ultrasonic diagnostics is ultrasonic endoscopes used in medical field.

Ultrasonic diagnostic apparatuses are used not only in the medical field but also in industrial fields in order to make a diagnosis on a presence or absence of defections such as a flaw, a crack, and a hollow appeared on a subject (sample). These ultrasonic diagnostic apparatuses are known as nondestructive inspection apparatuses and nondestructive flaw detection apparatuses.

Also known is an analytic method using a so-called V(z) curve, in which ultrasonic waves are irradiated to an object (sample) to evaluate an acoustic property of the object, thereby quantifying an elastic property of the object or evaluating structure of a thin film. Ultrasonic microscopes are known as such apparatuses for analyzing property of the object from the V(z) curve.

These ultrasonic diagnostic apparatuses and ultrasonic microscopes are provided with an ultrasonic transducer for converting electric signals into ultrasonic waves to transmit the ultrasonic waves and for receiving the ultrasonic waves to convert the ultrasonic waves into electric signals.

Conventionally, a piezoelectric element such as a ceramic piezoelectric material PZT (lead zirconate titanate) has been mainly used as the ultrasonic transducer. However, in recent years, attention is focused on a capacitive ultrasonic transducer (Capacitive Micromachined Ultrasonic Transducer; hereinafter referred to as a c-MUT) manufactured using a micromachining technology as disclosed in Japanese Unexamined Patent Application Publication No. 2005-510264.

The c-MUT is configured by including a pair of plate electrodes (parallel plate electrodes) facing each other sandwiching an air gap portion therebetween, and transmits and receives ultrasonic waves by vibration of a film (membrane) including one of the pair of electrodes. Since the c-MUT converts ultrasonic signals into electric signals based on a change in capacitance between the pair of electrodes at the time of receiving ultrasonic waves, it is required to continuously supply a DC bias voltage, which is a relative high voltage, between the pair of electrodes during the reception of ultrasonic waves.

In order to solve the problem, Japanese Patent Application Laid-Open Publication No. 2-52599 discloses a c-MUT (capacitive ultrasonic transducer) which unnecessitates application of a DC bias voltage by providing an electret (electret insulating film) between a pair of electrodes. In addition, in Japanese Unexamined Patent Application Publication No. 2005-506783 discloses an ultrasonic transducer including an electreted film provided directly on a pair of electrodes, in other words, on a transmitting side of ultrasonic waves.

SUMMARY OF THE INVENTION

In order to achieve the above object, an ultrasonic transducer of the present embodiment comprises: a transducer cell including: a first electrode, a vibration membrane disposed on the first electrode, separated by an air gap portion; and a second electrode supported by the vibration membrane; a first conductive layer electrically connected to the first electrode; a second conductive layer disposed facing the first conductive layer and electrically connected to the second electrode; an electret for retaining a charge and applying a predetermined potential difference between the first electrode and the second electrode, the electret being disposed in a region between the first conductive layer and the second conductive layer, where at least a part of the electret do not overlap with the transducer cell when viewed from a transmitting direction of ultrasonic waves generated by vibration of the vibration membrane.

The above and other objects, features and advantages of the invention will become more clearly understood from the following description referring to the accompanying drawings.

DETAILED DESCRIPTION OF PREFERRED EMBODIMENTS

Below, preferred embodiments of the present invention will be described with reference to the drawings. Note that, in each of the drawings referred to in the description below, scale sizes are differentiated for each component in order to show each component in a recognizable size on the drawings. The present invention is not limited only to the number, the shape and the size ratio of the components, and the relative positional relationship among the components illustrated in these drawings.

First Embodiment

Hereinafter, the first embodiment of the present invention is described with reference to FIGS. 1 to 8.

Figure 1:
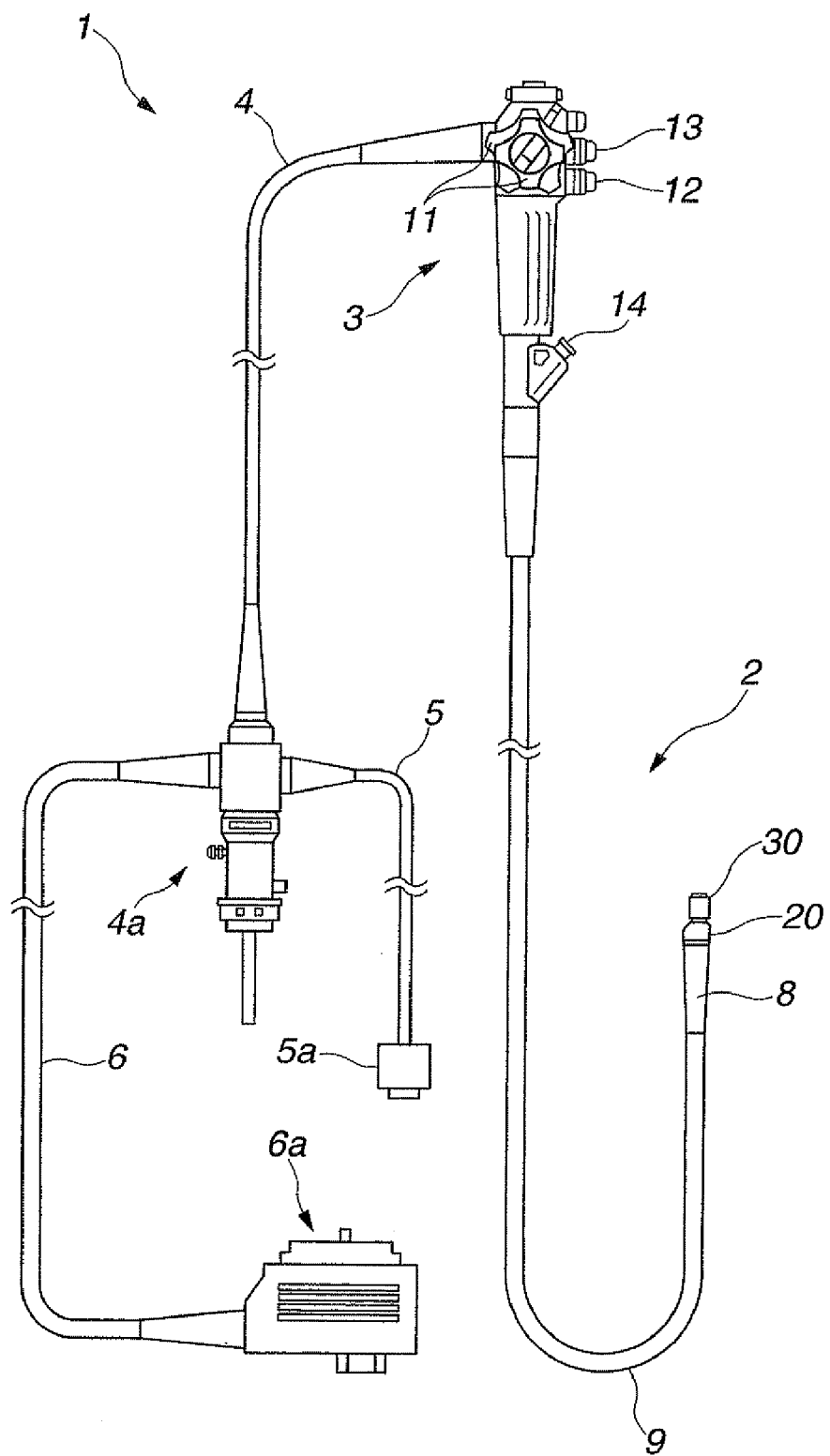
FIG. 1 is an illustration diagram showing a schematic configuration of an ultrasonic endoscope
Figure 2:
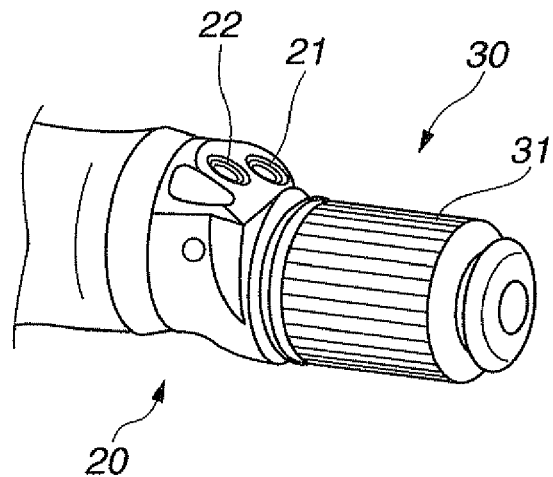
FIG. 2 is a perspective view showing a configuration of a distal end part of the ultrasonic endoscope
Figure 3:
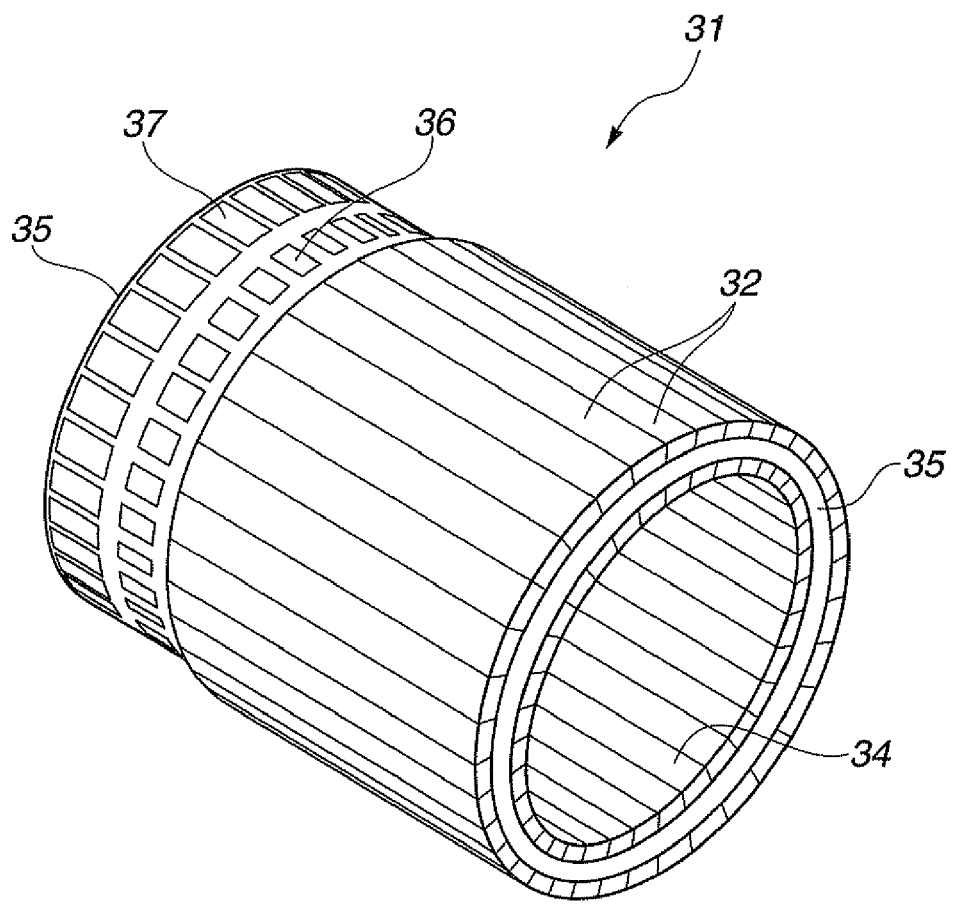
FIG. 3 is a perspective view of a transducer array.

FIG. 1 is an illustration diagram showing a schematic configuration of an ultrasonic endoscope. FIG. 2 is a perspective view showing a configuration of a distal end part of the ultrasonic endoscope. FIG. 3 is a perspective view of a transducer array.

In the present embodiment, description is made on an example in which the present invention is applied to an ultrasonic endoscope as an ultrasonic diagnostic apparatus. As shown in FIG. 1, an ultrasonic endoscope 1 of the present embodiment is mainly configured by an elongated insertion portion 2 to be inserted in a body cavity, an operation portion 3 positioned on a proximal end of the insertion portion 2, and a universal cord 4 extending from a side portion of the operation portion 3.

The universal cord 4 is provided at a proximal end thereof with an endoscope connector 4a connected to a light source device not shown. From the endoscope connector 4a are extended an electric cable 5 detachably connected to a camera control unit not shown through an electric connector 5a and an ultrasonic cable 6 detachably connected to an ultrasonic observation apparatus not shown through an ultrasonic connector 6a.

The insertion portion 2 is configured by including in the following order from a distal end side, a distal end rigid portion 20 formed of a rigid resin member; a bendable bending portion 8 positioned on a rear end of the distal end rigid portion 20; and a flexible tube portion 9 having a small diameter, a long length and flexibility, which is positioned on a rear end of the bending portion 8 and extended to a distal end portion of the operation portion 3. In addition, the distal end rigid portion 20 is provided at the distal end side thereof with an ultrasonic transmitting/receiving portion 30, to be detailed later, for transmitting and receiving ultrasonic waves.

The operation portion 3 is provided with: an angle knob 11 for bending and controlling the bending portion 8 in desired directions; an air/water feeding button 12 for performing air-feeding and water-feeding operations; a suction button 13 for performing a sucking operation; a treatment instrument insertion port 14 serving as an entrance for a treatment instrument to be introduced in a body cavity, and the like.

As shown in FIG. 2, the distal end rigid portion 20 is provided with: an illumination lens (not shown) configuring an illumination optical portion for irradiating illumination light to an observation region; an objective lens 21 configuring an observation optical portion for capturing an optical image of the observation region; a suction/forceps port 22 serving as an opening from which a resected region is sucked and a treatment instrument is projected; and an air/water feeding port (not shown) for feeding air and water.

The ultrasonic transmitting/receiving portion 30 provided at the distal end of the distal end rigid portion 20 includes a transducer array 31, a driving circuit 34, and an FPC 35, as shown in FIG. 3. The FPC 35 is a wiring substrate having flexibility (flexible wiring substrate) including mounting surfaces formed on both surfaces thereof. The FPC 35 is disposed in the ultrasonic transmitting/receiving portion 30 in such a manner as to be wound in a substantially cylindrical shape around an axis, as a central axis, substantially parallel to an insertion axis of the distal end rigid portion 20.

The transducer array 31 as the ultrasonic transducer array is provided on an outer circumferential surface of the cylindrically-shaped FPC 35. The transducer array 31 includes a plurality of transducer units 32 as the ultrasonic transducers of the present embodiment which are aligned on the outer circumferential surface of the FPC 35 in a circumferential direction. The transducer units 32 have a substantially rectangular shape when viewed from a normal line direction of the outer circumferential surface of the FPC 35, and are aligned at equal intervals on the outer circumferential surface of the cylindrically-shaped FPC 35, with the lateral direction being the circumferential direction. The transducer array 31 is configured of several tens to several hundreds of transducer units 32, for example, and the transducer array 31 of the present embodiment includes one hundred and twenty-eight transducer units 32. Each of the transducer units 32 includes forty-eight transducer elements 33.

Though details will be described later, the transducer units 32 of the present embodiment are capacitive ultrasonic transducers formed on a silicon substrate composed of low-resistance silicon semiconductors by the micromachining technology and belong to the technical field of so-called MEMS (Micro Electro Mechanical Systems). Such a capacitive ultrasonic transducer formed using the micromachining technology is generally referred to as c-MUT (Capacitive Micromachined Ultrasonic Transducer).

In the transducer array 31 of the present embodiment, the plurality of transducer elements 33 provided in one piece of transducer unit 32 configure a minimum driving unit for transmitting and receiving ultrasonic waves. The transducer elements 33 each transmit ultrasonic waves in the normal line direction of the mounting surface of the FPC 35, that is, in an outward radial direction of the cylindrically-shaped FPC 35.

On the other hand, a plurality of driving circuits 34 are mounted on an inner circumferential surface of the cylindrically-shaped FPC 35, that is, on a mounting surface which is on the opposite side of the mounting surface on which the transducer array 31 is mounted. Each of the driving circuits 34 includes electrical circuits such as a pulser, a selection circuit, and the like for driving the transducer element 33 and is electrically connected to the each of the transducer elements 33.

In addition, the driving circuits 34 are electrically connected to a plurality of signal electrodes 36 and ground electrodes 37 which are formed on the outer circumferential surface of the cylindrically-shaped FPC 35. The signal electrodes 36 and the ground electrodes 37 are connected to a coaxial cable. The coaxial cable is inserted through the ultrasonic cable 6 and one end thereof is electrically connected to the ultrasonic connector 6a and the other end thereof is electrically connected to the signal electrodes 36 and the ground electrodes 37. Thus, the driving circuits 34 are electrically connected to the ultrasonic observation apparatus.

The ultrasonic transmitting/receiving portion 30 having the above-described configuration can perform an electronic radial scan capable of sector scanning, for radially transmitting and receiving ultrasonic waves on a plane substantially perpendicular to the insertion axis of the distal end rigid portion 20 as a base by the two-dimensional transducer array 31 disposed on the outer circumferential surface of the cylindrically-shaped FPC 35.

Figure 4:
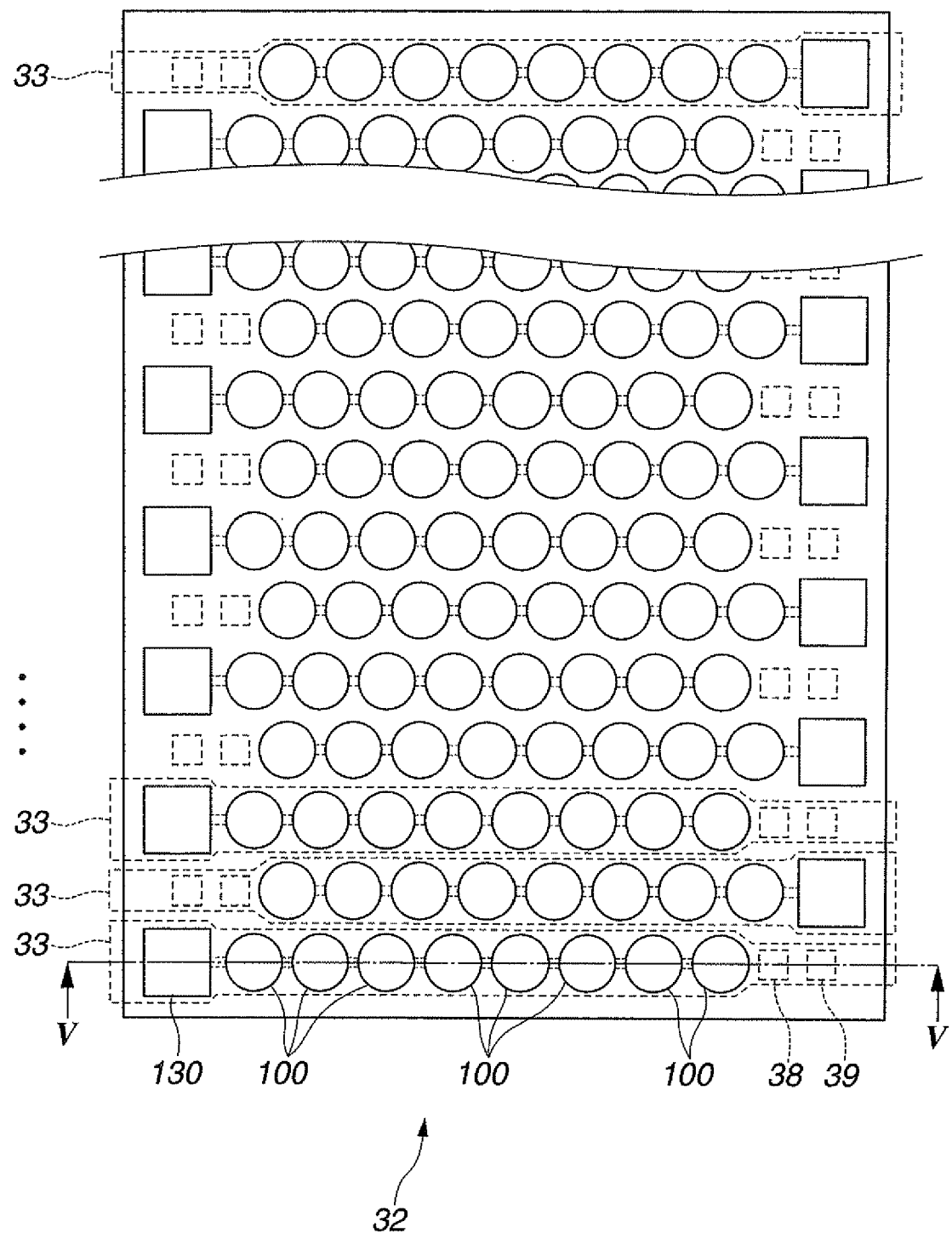
FIG. 4 is a top view of a transducer unit viewed from a transmitting direction of ultrasonic waves.
Figure 5:
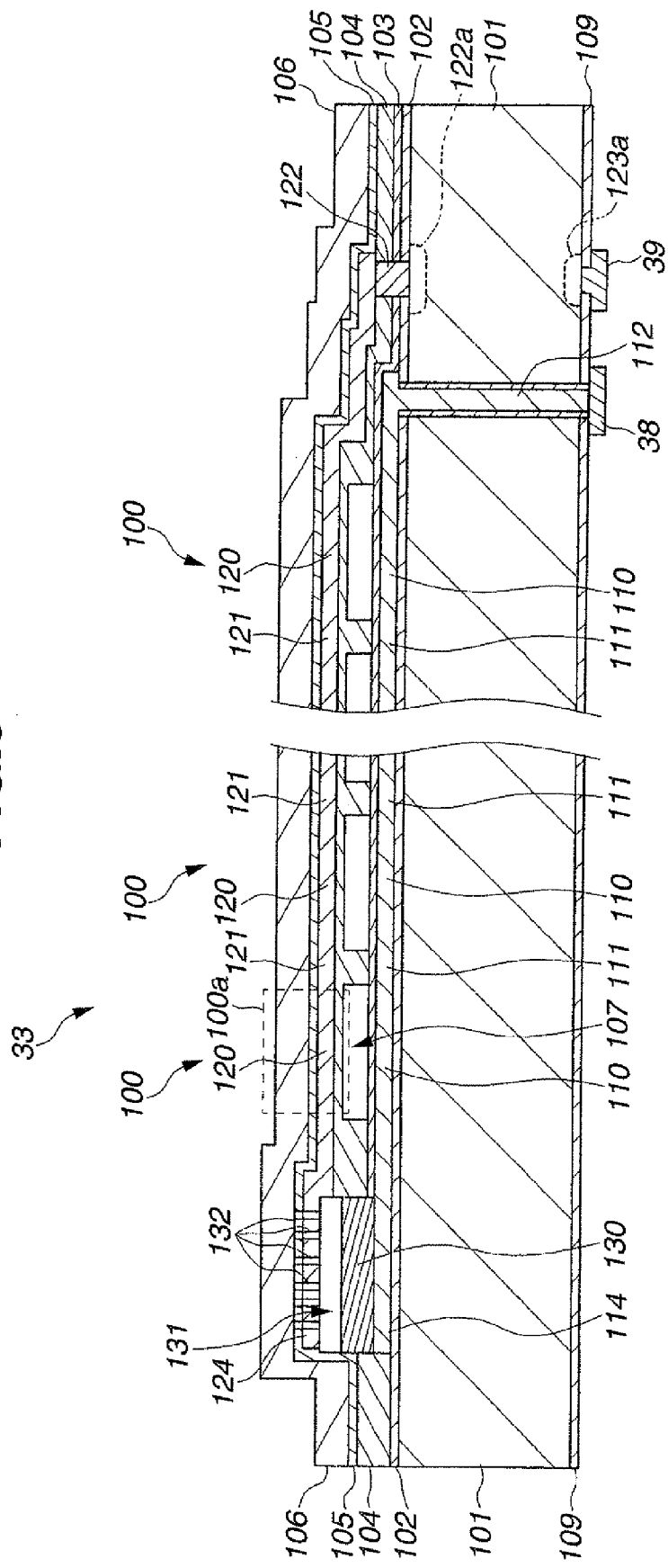
FIG. 5 is a cross-sectional view along the V-V line in FIG. 4.
Figure 6:
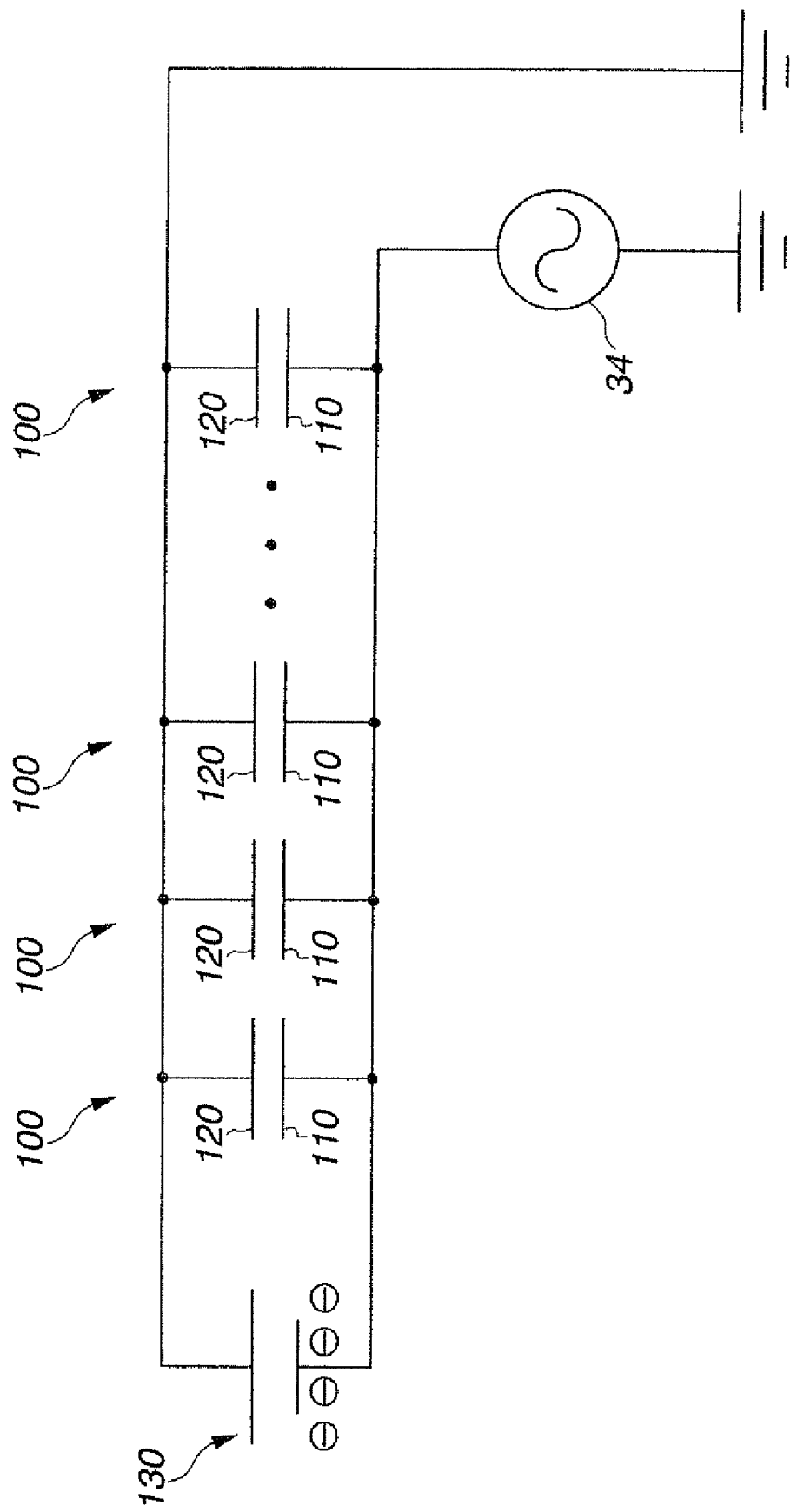
FIG. 6 is an equivalent circuit diagram of a transducer element.
Figure 7:
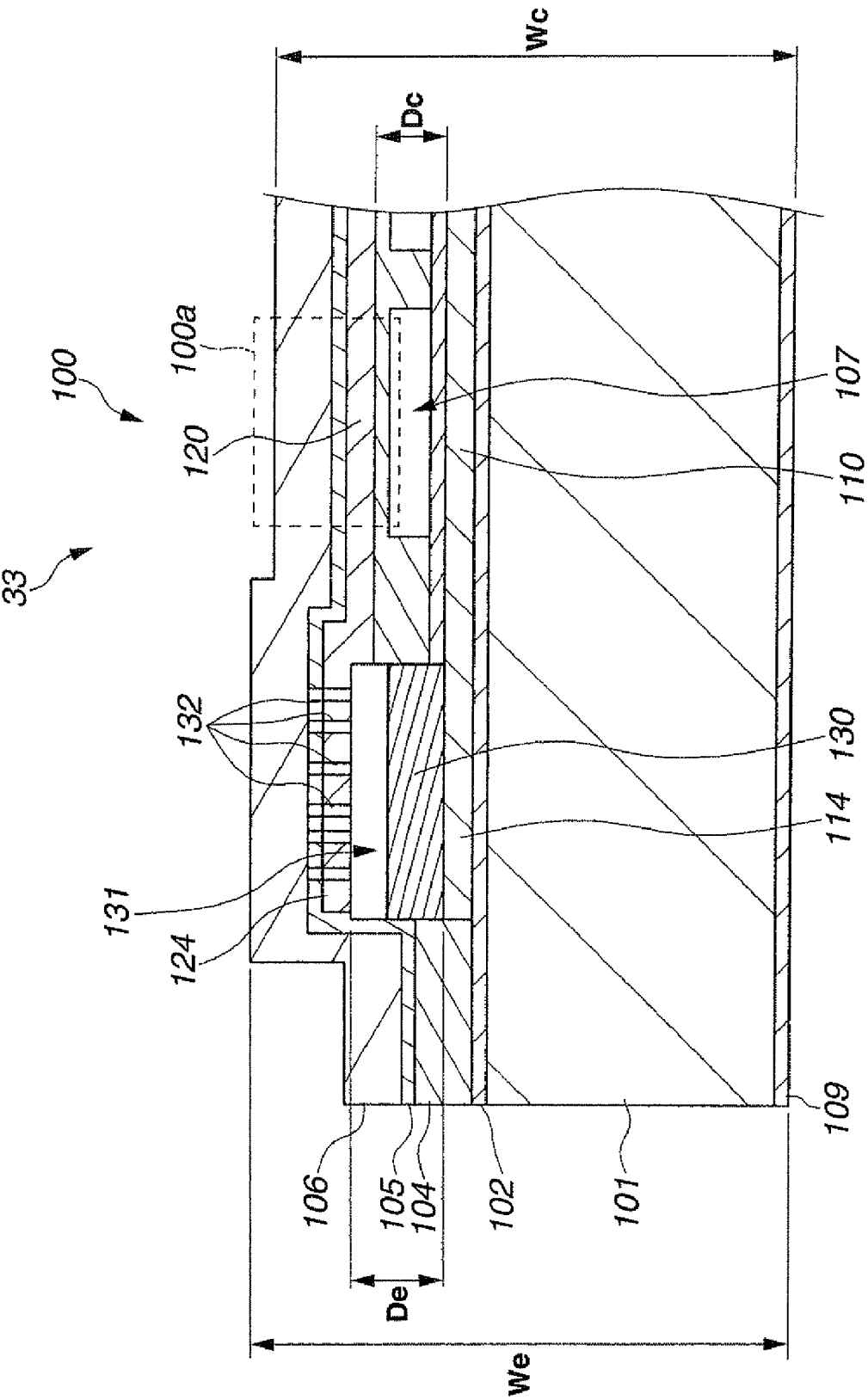
FIG. 7 is a partial cross-sectional view of a region where an electret of the transducer element is formed.

Next, description is made below on a detailed configuration of the transducer unit 32 as the capacitive ultrasonic transducer of the present embodiment, with reference to FIGS. 4 to 7. FIG. 4 is a top view of the transducer unit 32 viewed from the transmitting/receiving side of ultrasonic waves. That is, in FIG. 4, ultrasonic waves are transmitted in a direction perpendicular to and away from the paper surface. FIG. 5 is a cross-sectional view along the V-V line in FIG. 4. FIG. 6 is an equivalent circuit diagram of a transducer element 33. FIG. 7 is a partial cross-sectional view of a region where an electret of the transducer element is formed.

As shown in FIG. 4, the transducer unit 32 of the present embodiment is configured by the plurality of aligned transducer elements 33. In FIG. 4, an elongated region surrounded by a dashed line represents one piece of transducer element 33.

The transducer element 33 includes a plurality of transducer cells 100. In addition, the transducer element 33 includes an electret 130, a signal electrode pad 38, and a ground electrode pad 39, which are electrically connected to each of the plurality of transducer cells 100 configuring the transducer element 33.

In the present embodiment, the transducer element 33 includes: eight transducer cells 100 linearly aligned in a longitudinal direction of the elongated region; and one piece of the electret 130 disposed at one end of the elongated region and electrically connected in parallel to all of the eight transducer cells 100.

In the same transducer element 33, all of the transducer cells 100 are electrically connected in parallel to one another, and inputted with driving signals from the ultrasonic observation apparatus through the signal electrode pad 38, thereby simultaneously transmitting ultrasonic waves having the same phase.

As shown in FIG. 5, the transducer element 33 of the present embodiment is a capacitive ultrasonic transducer having, on the silicon substrate 101 composed of the low-resistance silicon semiconductors, a layer structure formed by the micromachining technology using a semiconductor process and the like.

Note that, in the description of the layer structure below, as for the up-down relationship of the layers, the up direction is assumed to be a direction away from the surface of the silicon substrate 101 in the normal line direction. For example, in the cross-sectional view in FIG. 5, an upper electrode 120 is assumed to be disposed above a lower electrode 110. In addition, a thickness of each layer indicates a dimension of each layer in the normal line direction of the surface of the silicon substrate 101. Furthermore, in the description below, for descriptive convenience, of the surfaces of the silicon substrate 101, the surface on which the transducer cells 100 are formed is referred to as a cell forming surface, and the surface opposite to the surface on which the transducer cells 100 are formed is referred to as a rear surface.

The silicon substrate 101 is made of conductive low-resistance silicon. On both surfaces of the silicon substrate 101, a first insulating film 102 and a rear surface insulating film 109, each a silicon oxide film having electrical insulation, are respectively formed. The first insulating film 102 and the rear surface insulating film 109 are high-temperature oxide films formed by thermal-oxidizing the silicon substrate 101. Note that, the first insulating film 102 and the rear surface insulating film 109 may be silicon nitride films.

First, a structure of the transducer cell 100 is described in detail below.

The transducer cell 100 is configured by including the lower electrode 110 (a first electrode) and the upper electrode 120 (a second electrode) which are a pair of parallel plate electrodes facing each other through a cavity 107 as a substantially columnar air gap portion. The transducer element 33 configured by including the transducer cells 100 transmits and receives ultrasonic waves by vibration of a membrane 100a (vibration membrane) which is a film-shaped structure with elasticity and includes the upper electrode 120 of the transducer cell 100.

On the first insulating film 102 is formed the lower electrode 110 which is a conductive layer substantially circular-shaped when viewed from above. The lower electrode 110 is formed by sputtering Mo (molybdenum) into a film, and patterning the film. The lower electrodes 110 of the transducer cells 100 adjacent to each other when viewed from above are electrically connected to each other by a lower electrode wiring 111.

Note that, it is preferable that the material configuring the lower electrode 110 which is a lower layer part of the layer structure and formed on the silicon oxide film is, aside from the Mo, for example, high melting point metals such as W (tungsten), Ti (titanium), and Ta (tantalum), or an alloy of such metals. However, the material is not limited to these, as long as the high-temperature thermal processing can be avoided in subsequent processes, and may be Al (aluminum), Cu (copper), or the like. In addition, the lower electrode 110 may have a multi-layer structure in which two or more kinds of conductive materials are layered.

A wafer-through electrode 112 formed by penetrating the silicon substrate 101 is provided, for each transducer element 33, on an end portion of the transducer element 33 having the elongated shape when viewed from above, which is on the opposite side of the end portion on which the electret 130 is disposed. The wafer-through electrode 112 is electrically insulated from the silicon substrate 101, and electrically connected to the lower electrodes 110 and to the signal electrode pad 38 formed on the rear surface insulating film 109.

That is, all the lower electrodes 110 in the same transducer element 33 are electrically connected to the signal electrode pad 38 formed on the rear surface of the silicon substrate 101 through the lower electrode wiring 111 and the wafer through electrode 112.

A second insulating film 103 having electrical insulation is formed on the lower electrode 110 so as to cover the lower electrode 110. The second insulating film 103 is a silicon oxide film in the present embodiment and is formed by the plasma CVD method. Note that the second insulating film 103 may be a silicon nitride film, a hafnium nitride (HfN), a hafnium oxynitride (HfON), or the like.

A third insulating film 104 having electrical insulation is formed on the second insulating film 103 over the cavity 107. The third insulating film 104 is a silicon oxide film in the present embodiment and is formed by the plasma CVD method. Note that the third insulating film 104 may be a silicon nitride film.

The cavity 107 as a hermetically-sealed air gap layer in an atmospheric pressure, a pressurized, or a depressurized state is formed between the second insulating film 103 and the third insulating film 104. Here, the depressurized state indicates a state where the pressure is lower than the atmospheric pressure, and also includes a so-called vacuum state. The cavity 107 has a substantially columnar shape and is provided substantially concentrically with the lower electrode 110 when viewed from above.

In the present embodiment, the cavity 107 is formed by the sacrificial layer etching as a known technology, and a sacrificial layer removal hole for communicating inside of the cavity 107 with the upper layer of the third insulating film 104 which are used at the time of sacrificial layer etching is sealed by a plug not shown. Note that the cavity 107 may be formed by a method of joining together wafers subjected to mechanical or chemical microfabrication.

On the third insulating film 104 is formed the upper electrode 120 which is a substantially circular-shaped conductive layer when viewed from above. The upper electrode 120 is provided substantially concentrically with the lower electrode 110 when viewed from above, that is, on a position facing the lower electrode 110. In the present embodiment, the upper electrode 120 is formed by sputtering Al (aluminum) into a film, and patterning the film.

The upper electrodes 120 of the transducer cells 100 adjacent to each other when viewed from above are electrically connected to each other by an upper electrode wiring 121. Note that the material configuring the upper electrode 120 may be, for example, Cu, W, Ti, Ta, and the like, aside from Al, as long as the material has a conductive property. In addition, the upper electrode 120 may have a multi-layer structure in which two or more kinds of conductive materials are layered.

The upper electrode wiring 121 is electrically connected to a through electrode 122 on the end portion of the transducer element 33 having the elongated shape when viewed from above, which is on the opposite side of the end portion on which the electret 130 is disposed. The through electrode 122 penetrates the first insulating film 102, the second insulating film 103, and the third insulating film 104, and is formed in the same process as the forming process of the upper electrode 120 and the upper electrode wiring 121. The through electrode 122 is electrically connected to the silicon substrate 101 through an ohmic contact region 122a.

In addition, the ground electrode pad 39 is formed on the rear surface insulating film 109. The ground electrode pad 39 is electrically connected to the silicon substrate 101 through an ohmic contact region 123a.

That is, all the upper electrodes 120 in the same transducer element 33 are electrically connected to the ground electrode pad 39 formed on the rear surface of the silicon substrate 101, through the upper electrode wiring 121, the through electrode 122, and the silicon substrate 101.

A protective film 105 having electrical insulation is formed on the upper electrode 120. The protective film 105 is a silicon nitride film in the present embodiment and is formed by the plasma CVD method. Note that, the protective film 105 may be configured of a silicon oxide film, hafnium nitride (HfN), hafnium oxynitride (HfON), and the like, aside from the silicon nitride. HfN and HfON are particularly preferable for the protective film, since a high-density film can be obtained.

Furthermore, a paraxylylene resin film 106 having water-resistance, chemical-resistance, or the like, and is excellent in biocompatibility and electrical insulation is formed on the protective film 105.

The transducer unit 32 is mounted on the FPC 35, by a known method such as a solder joining, an anisotropic conductive film joining, or an ultrasonic joining. Thus, the above-described transducer cells 100 of the transducer element 33 are electrically connected to the driving circuit 34 mounted on the opposite side of the FPC 35 through the signal electrode pad 38 and the ground electrode pad 39.

By providing the signal electrode pad 38 and the ground electrode pad 39 on the rear surface side of the transducer cells 100, mounting area can be reduced, which can reduce the length of the distal end rigid portion 20 and improve the operability of the ultrasonic endoscope 1.

Note that, in the above-described configuration, the lower electrode 110, the upper electrode 120, and the cavity 107 have substantially circular shapes when viewed from above. However, the shapes are not limited to those in the present embodiment, and, for example, may be polygonal shapes such as hexagonal shape, rectangular shape, or other shapes. The dimensions of the membrane 100a and the cavity 107 are determined depending on the wavelength and output of the ultrasonic waves used at the time of observation.

Next, detailed description is made on the configuration of the region where the electret 130 of the ultrasonic transducer of the present embodiment is disposed.

In the present embodiment, the electret 130 as the charge retention means is disposed, as described above, at the end portion of the transducer element 33 having the elongated shape when viewed from above. The electret 130 has a function of permanently retaining positive or negative polarity charge.

The electret 130 in the present embodiment is made of an inorganic film. To be more precise, the electret 130 is formed by charging the silicon oxide film formed by the plasma CVD method and the like, by a corona discharge. Note that the electret 130 may be made of other inorganic films such as a silicon nitride film or Hf (hafnium) oxide like HfO2 film or HfAl 205 film. In addition, the electret 130 may be formed by layering a plurality of kinds of the above-described inorganic films.

As shown in the equivalent circuit diagram in FIG. 6, in one transducer element 33, the negative charge retaining side of the electret 130 is electrically connected to each of the lower electrodes 110 of the plurality of transducer cells 100. Since the upper electrode 120 of the transducer cell is grounded, the electret 130 applies a potential difference between the lower electrode 110 and the upper electrode 120 as a pair of electrodes of the transducer cell 100.

That is, the transducer cell 100 is electrically equivalent to the state where the DC bias voltage is applied between the lower electrode 110 and the upper electrode 120. As a result, the transducer element 33 as the ultrasonic transducer of the present embodiment is capable of transmitting and receiving ultrasonic waves without a need of application of DC bias voltage from outside.

Therefore, the ultrasonic diagnostic apparatus provided with the transducer elements 33 as the ultrasonic transducers of the present embodiment does not need a circuit or a wiring for applying the DC bias voltage as required in the conventional c-MUT, which can reduce the size of the apparatus. In addition, the values of the currents flowing through the DC bias voltage source and the wiring are reduced, which decreases the power consumption. With this configuration, the size of the driving circuit can be further reduced, thereby preventing property fluctuation of the transducer cells due to heat generated by the driving circuit.

As specifically shown in the cross-sectional view in FIG. 7, the electret 130 of the present embodiment is interposed between a lower conductive layer 114 (a first conductive layer) electrically connected to the lower electrodes 110 of the transducer cells 100 and an upper conductive layer 124 (a second conductive layer) electrically connected to the upper electrodes 120. Note that, in the present embodiment, the lower conductive layer 114 is a conductive layer made of Mo formed by the same semiconductor process as that of forming the lower electrodes 110. The upper conductive layer 124 is a conductive layer made of Al formed by the same semiconductor process as that of forming the upper electrodes 120.

In addition, an air gap portion 131 as an insulating layer is interposed between the electret 130 and the upper conductive layer 124. In the present embodiment, the air gap portion 131 is formed by the sacrificial layer etching as a known technology. Note that the air gap portion 131 may be other insulating film, for example, a silicon oxide film or silicon nitride film as long as the material can electrically insulate the electret 130 from the upper conductive layer 124.

On the upper conductive layer 124, the protective film 105 having electrical insulation is formed similarly as in the transducer cells 100 part. The protective film 105 is a silicon nitride film in the present embodiment as described above.

Furthermore, in the upper conductive layer 124 and the protective film 105 that are disposed above the electret 130 are drilled a myriad of microscopic through holes 132 penetrating the upper conductive layer 124 and the protective film 105 in a thickness direction. The through holes 132 are formed on the upper conductive layer 124 and the protective film 105 only in a region overlapping with the electret 130 when viewed from above. In the present embodiment, the through holes 132 have a diameter of micrometer order (several micrometers of diameter) and are scattered in a random manner at a predetermined distribution density.

Note that the through holes 132 drilled in the upper conductive layer 124 and the protective film 105 are not limited to the configuration in the present embodiment, and may be formed by being aligned regularly, for example, in rows and columns.

The paraxylylene resin film 106 is formed on the protective film 105 in the similar manner as in the transducer cells 100 part.

In addition, as shown in FIG. 7, in the transducer element 33, the region where the electret 130 is disposed is formed to be projected upward (in the transmitting direction of ultrasonic waves) more than the region where the transducer cells 100 are formed. To be more precise, the thickness We of the region of the transducer element 33 where the electret 130 is disposed becomes larger than the thickness We of the region of the transducer element 33 where the transducer cells 100 are formed.

Thus, with the configuration in which the region adjacent to the transducer cells 100 projects in the transmitting direction of ultrasonic waves more than the region where the transducer cells 100 are formed, the transducer element 33 of the present embodiment can prevent destruction of the membranes 100a of the transducer cells 100 resulting from a contact with other objects.

Furthermore, in the present embodiment, a distance De between the upper conductive layer 124 and the lower conductive layer 114, which are parallel plate electrodes facing each other in the region where the electret 130 is formed, is formed to be larger than a distance DC between the upper electrode 120 and the lower electrode 110 of the transducer cell 100. Accordingly, it is possible to restrain generation of parasitic capacitance in the region not contributing to the transmitting and receiving of ultrasonic waves, and thereby increase a driving efficiency of the ultrasonic unit.

Here, the charging processing by the corona discharge on the electret 130 in the transducer element 33 as the ultrasonic transducer of the present embodiment, is performed in a state where the air gap portion 131, the upper conductive layer 124 and the protective film 105 are formed on the silicon oxide film as the electret 130, and the through holes 132 are formed to penetrate the upper conductive layer 124 and the protective film 105 in the thickness direction. The electrode 114 is normally used for inputting ultrasonic transmitting/receiving signals, but used as a counter electrode for corona discharge in the charging processing by the corona discharge.

That is, the charging processing by the corona discharge on the electret 130 is performed after the semiconductor process of forming the layer structure after forming the electret 130 is all finished, in a state where at least a part of the electret 130 is exposed upward through the through holes 132.

Then, after the charging processing performed on the electret 130, by forming the paraxylylene resin film 106 by a spin coat method, the structure on the cell forming surface side of the transducer element 33 is completed.

Below, description is made on the effects of the ultrasonic transducer and the ultrasonic diagnostic apparatus of the present embodiment that have the above-described configuration.

In the transducer element 33 of the present embodiment, the electret 130 is disposed in a region not overlapping with and separated from the transducer cell 100, when viewed from the transmitting direction of ultrasonic waves, that is, the layer direction of the lower electrode 110 and the upper electrode 120 as a pair of electrodes of the transducer cell 100. Therefore, in the transducer element 33 of the present embodiment, the thickness of the electret 130 and the distance between the lower electrode 110 and the upper electrode 120 can be set independently.

For example, compared with a conventional capacitive ultrasonic transducer including an electret disposed between a pair of parallel plate electrodes, in the transducer element 33 of the present embodiment, the distance (gap) between the pair of parallel plate electrodes (the lower electrode 110 and the upper electrode 120 in the present embodiment) can be made smaller and the electret 130 as the charge retention means can be made thicker.

Therefore, according to the present embodiment, the distance between the lower electrode 110 and the upper electrode 120 is made smaller than in the conventional transducer to increase the capacitance between the electrodes, which can improve the sound pressure of the transmitted ultrasonic waves and the sensitivity to the received ultrasonic waves and make the electret 130 to have a thickness to allow permanent and stable charge retention.

In addition, in the transducer element 33 of the present embodiment, the lower electrode 110 and the upper electrode 120, and the electret 130 are not disposed in a layered manner in the thickness direction, thereby enabling the transducer element 33 to be thinner than the conventional capacitive ultrasonic transducer.

Similarly, compared with a conventional capacitive ultrasonic transducer configured by layering a transducer cell and an electret in the thickness direction, the transducer element 33 of the present embodiment can be configured to be thinner in the ultrasonic wave transmitting direction.

Therefore, the transducer element 33 as the ultrasonic transducer of the present embodiment is thinner and has a higher sound pressure of the transmitted ultrasonic waves and a higher sensitivity to the received ultrasonic waves than the conventional transducer, and in addition, can permanently maintain the characteristics.

In other words, at the time of exerting a predetermined sound pressure of the transmitted ultrasonic waves and sensitivity to the received ultrasonic waves, the present embodiment realizes the ultrasonic transducer which maintains the initial performance over a long period of time, and is thinner and can be driven at lower voltage compared with the conventional one.

In addition, the present embodiment allows the ultrasonic diagnostic apparatus including the transducer element 33 which is thin and can be drive at low voltage to have a longer operation life and smaller size than the conventional one. For example, with the ultrasonic endoscope 1 shown in FIG. 1, the outer diameter of the transducer array 31 can be made smaller than the conventional one, which realizes a diagnosis at low burden for the patient.

Furthermore, in the transducer element 33 of the present embodiment, the upper conductive layer 124 and the protective film 105 disposed in the upper layer of the electret 130 have the through holes 132 formed so as to penetrate the upper conductive layer 124 and the protective film 105 in the thickness direction. At the time that the forming processes of the upper conductive layer 124 and the protective film 105 are finished, since the electret 130 is disposed in the region separated from the transducer cells 100 when viewed from the transmitting direction of ultrasonic waves, at least a part of the electret 130 is exposed upward (the transmitting direction of ultrasonic waves) through the through holes 132.

In the transducer element 33 of the present embodiment having such a configuration, the process of performing the charging processing on the electret 130 by the corona discharge can be easily performed after the upper conductive layer 124 and the protective film 105 are formed. In this charging processing, not all of the charges generated by the corona discharge are retained by the upper conductive layer 124 as the conductive layer covering the electret 130, but a part of the charges reaches the electret 130 through the through holes 132. Then, after the charging processing on the electret 130 is finished, the forming process of the paraxylylene resin film 106 is performed and the structure on the cell forming surface side of the transducer element 33 is completed. Note that it is preferable that the paraxylylene resin includes fluorine (F), since its chemical resistance is high.

In other words, in the present embodiment, after all the layer structures formed by the semiconductor process have been formed, the charging processing on the electret 130 is performed. Therefore, after the charging processing has been performed on the electret 130, no process of heating the electret 130 up to a high temperature exists.

Generally, the electret as the charge retention means has such a property that the charge is discharged and the retaining charge amount decreases when the electret temperature is increased. For example, in the electret 130 of the present embodiment which is made of the silicon oxide film, when the electret temperature is increased to about not less than 400 degrees Celsius, decrease in charging amount occurs. Since the decrease in the charging amount retained by the electret 130 leads to a decrease in the direct-current voltage components to be applied between the lower electrode 110 and the upper electrode 120, in particular, the sensitivity to the received ultrasonic waves of the element 33 decreases.

For example, in a case of forming the conventional capacitive ultrasonic transducer having electret disposed between the pair of the parallel plate electrodes by the semiconductor process, if the processing performed at not less than 400 degrees Celsius is performed on the upper layer side electrodes and film formation of the insulating film after the charging processing has been performed on the electret, the charging amount of the electret decreases, thereby decreasing the sensitivity of the ultrasonic transducer. In order to address this problem, it may be possible to adopt a method of preventing the decrease in the charging amount of the electret by performing all the processes of manufacturing the ultrasonic transducer at a temperature not more than 400 degrees Celsius after the charging processing has been performed on the electret. However, since available film formation methods are limited, more manufacturing apparatuses are needed and the processes become complicated, which results in the problem of cost increase.

However, the transducer element 33 having the configuration of the present embodiment can be manufactured without heating the electret 130 subjected to the charging processing up to a temperature at which the charging amount retained by the electret 130 decreases.

Therefore, in the transducer element 33 as the ultrasonic transducer of the present embodiment, the retaining charging amount of the electret 130 can be increased more than that of the conventional one, so that the transducer element 33 has a higher sensitivity to the received ultrasonic waves when driven at a low voltage. Furthermore, since the transducer element 33 of the present embodiment does not require the semiconductor process performed at a relatively low temperature, for example, at a processing temperature not more than 400 degrees Celsius in the manufacturing process, the transducer element 33 can be manufactured at low cost by a more universal semiconductor manufacturing apparatus.

Note that in the above-described present embodiment, though it is described that the electret 130 is formed by performing charging processing on the single-layer or multilayer inorganic film such as a silicon oxide film, the configuration of the electret 130 is not limited to this.

For example, the electret 130 may be made of an organic film, and particularly, may be formed by charging the fluorocarbon resin which is generally called as FEP by the corona discharge, or configured of another organic film such as fluorocarbon resin other than FEP, polyimide, polypropylene, polymethylpentene, or the like.

The electrets made of these organic films have been conventionally used in other fields and known to be able to stably retain the charge over a long period of time. However, the electrets made of the organic films have such a property that the retaining charge amount decreases when heated to a high temperature, and in particular, the decrease in the retaining charge amount occurs at about 100 to 200 degrees Celsius which is lower than in the case of the electrets made of the inorganic films. Therefore, it has been difficult to apply the electrets made of the organic film to the capacitive ultrasonic transducer formed by the semiconductor process.

However, in the transducer element 33 of the present embodiment, since the charging processing on the electret is performed after the completion of the semiconductor process, as described above, even if the electret is configured of the organic film, the charge amount retained by the electret does not decrease.

Therefore, according to the present embodiment, the electret of the transducer element 33 can be configured of an organic film capable of stably retaining the charge over a longer period of time than the conventional one, which can provide a capacitive ultrasonic transducer having longer operation life than the conventional one.

In addition, in the above-described present embodiment, the electret 130 retaining negative charge is formed so as to contact the lower conductive layer 114 electrically connected to the lower electrode 110 of the transducer cell 100. Then, the air gap portion 131 is interposed between the electret 130 and the upper conductive layer 124.

Such a configuration is particularly effective in a case where the voltage signal outputted from the driving circuit 34 to be applied to the lower electrode 110 at the time of transmission of ultrasonic waves by the transducer element 33 has a negative polarity. This is because such a configuration allows the direct-current voltage components of the negative polarity to be applied between the lower electrode 110 and the upper electrode 120 by the electret 130, which can prevent the charge retained by the electret 130 from flowing out from the upper conductive layer 124 as the ground potential.

In addition, in order to more certainly ensure the charge retention by the electret 130, it is effective to cover the entire surface of the periphery of the electret 130 with an insulating film. Note that it is needless to say that the insulating film covering the entire surface of the periphery of the electret 130 may be divided into a plurality of insulating films.

Figure 8:
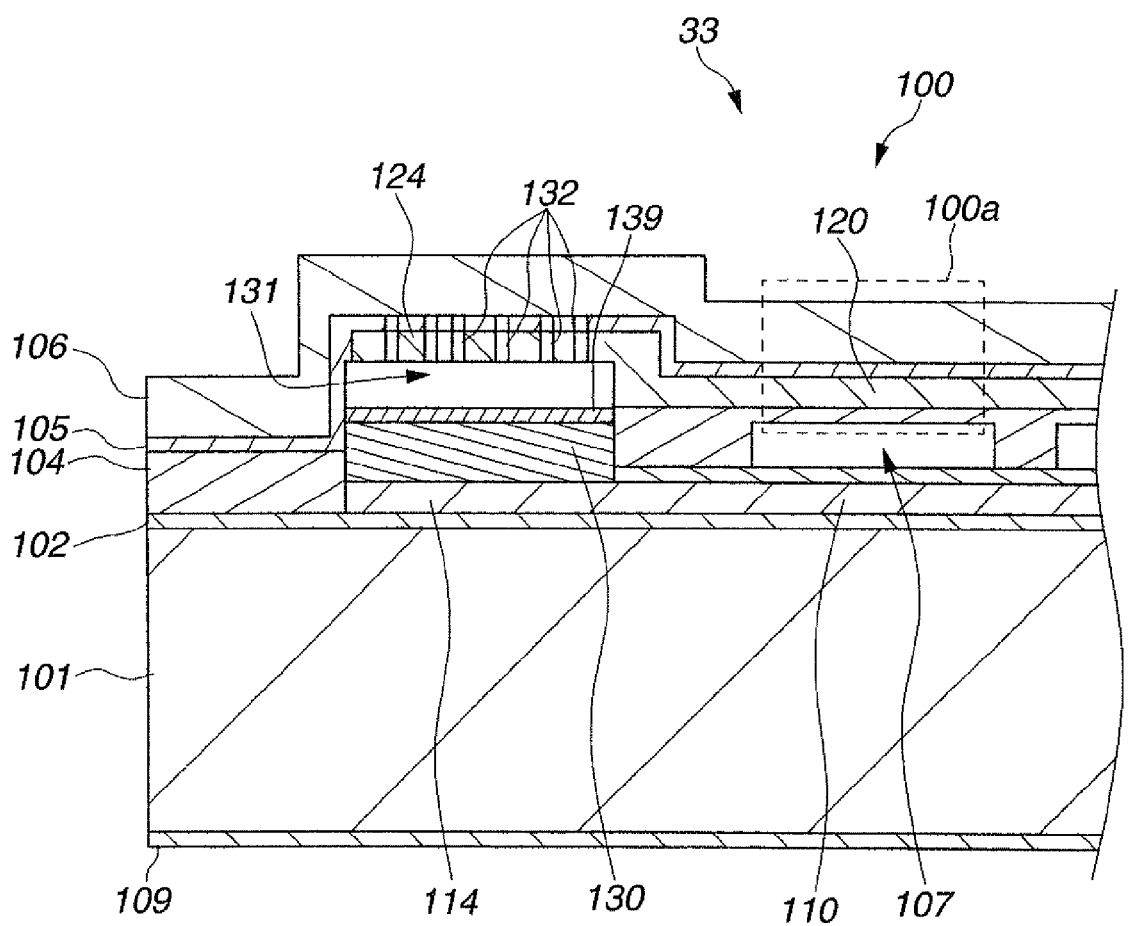
FIG. 8 is a partial cross-sectional view of a region where an electret according to a modified example of a first embodiment is formed.

For example, as shown in FIG. 8 as a modified example of the present embodiment, with the configuration in which the entire surface of the periphery of the electret 130 is covered with an insulating film by forming an insulating layer 139 on at least one of the lower layer side and the upper layer side of the electret 130, the charge retention by the electret 130 can be ensured more certainly.

In the modified example of the present embodiment shown in FIG. 8, when the electret 130 is configured of a silicon oxide film, it is preferable that the second insulating film 104, the protective film 105, and the insulating layer 139 are configured of a silicon nitride film.

Note that, depending on the polarity of the signal outputted from the driving circuit 34 and to which of the lower electrode 110 and the upper electrode 120 the signal is applied, the polarity of the charge retained by the electret 130 and the position where the air gap portion 131 is interposed are appropriately changed, and not limited to the above-described embodiment.

Furthermore, in an ultrasonic diagnostic apparatus configured by including an ultrasonic transducer, there are some cases that the ultrasonic transducer is covered with a shield layer as a conductive layer grounded electrically independently of the ultrasonic transducer, in order to shield the exogenous noise and improve the S/N ratio.

In a case where the shield layer is applied to the above-described present embodiment, if for example the process of covering the transducer element 33 with the shield layer is performed at a temperature at which the charge amount retained by the electret 130 decreases the through holes are formed on the region on the shield layer which overlaps with the electret 130, similarly on the upper conductive layer 124, and charging processing is performed on the electret 130 through the through holes.

For example, if the process of covering the transducer element 33 with the shield layer is performed at a temperature lower than the temperature at which the charge amount retained by the electret 130 decreases, it is neither necessary to form the shield layer after the charging processing has been performed on the electret 130, nor to form the through holes.

Note that, though the transducer element of the present embodiment is configured of the conductive silicon substrate 101 as the base material, the transducer element may be formed on a base material configured of an insulation material such as quartz, sapphire, crystal, alumina, zirconia, glass, resin, or the like, which has an electrical insulation.

In addition, though the ultrasonic endoscope of the present embodiment is described as one performing an electronic radial scan, the scanning method is not limited to this, and may be a linear scan, a convex scan, mechanical scan, and the like.

Figure 9:
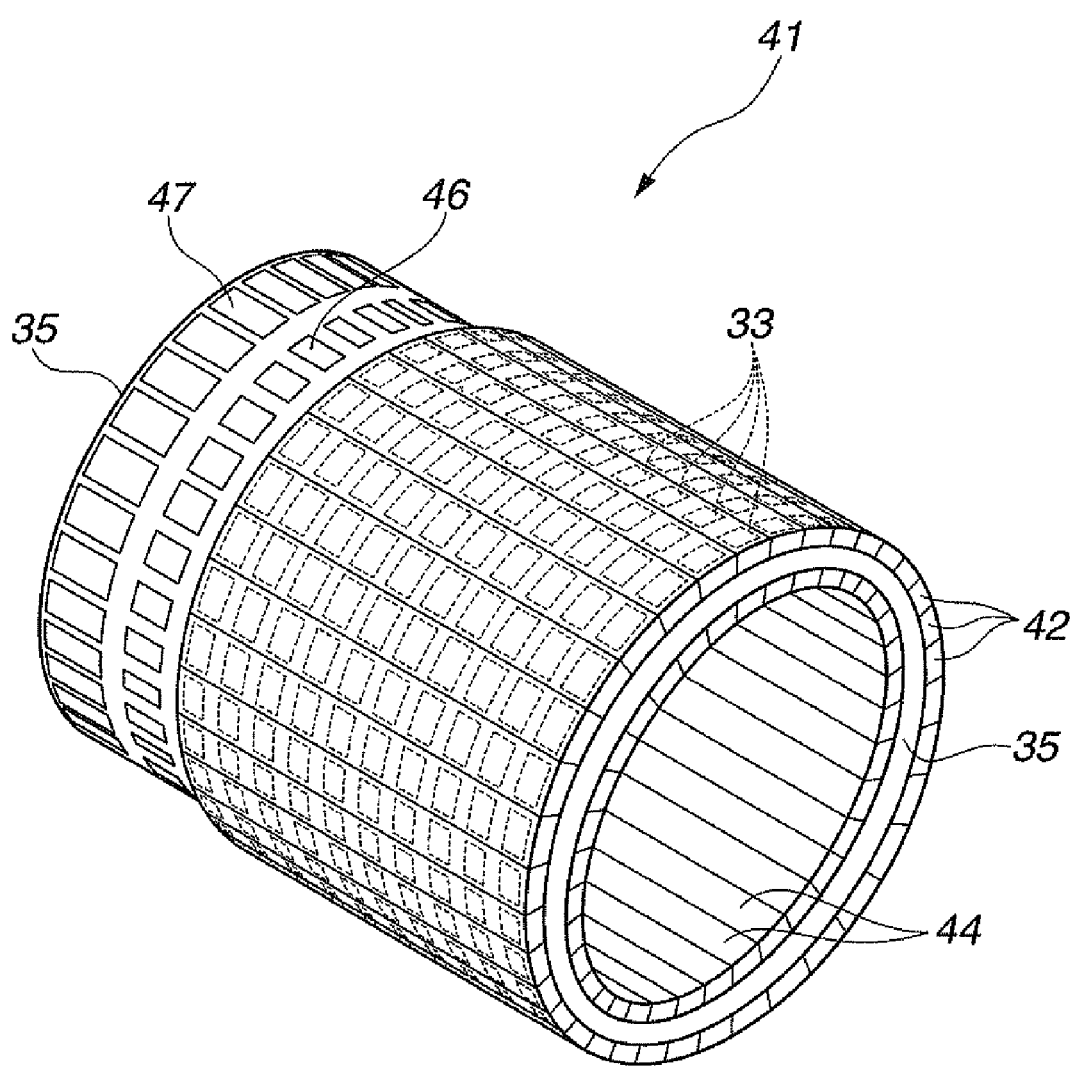
FIG. 9 is a view showing a modified example of the transducer array according to the first embodiment.

The transducer array may be configured as a two-dimensional array in which the minimum driving unit for transmitting and receiving ultrasonic waves is two-dimensionally aligned. An example of such a configuration is shown in FIG. 9 as one modified example of the present embodiment.

In the present modified example, a transducer array 41 as the two-dimensional ultrasonic transducer array is provided on the outer circumferential surface of the cylindrically-shaped FPC 35. The transducer array 41 is configured by including a plurality of transducer units 42 aligned on the outer circumferential surface of the FPC 35 in a circumferential direction. The transducer units 42 have a substantially rectangular shape when viewed from the normal line direction of the outer circumferential surface of the FPC 35, and are aligned at equal intervals on the outer circumferential surface of the cylindrically-shaped FPC 35, with the lateral direction as the circumferential direction. The transducer array 41 is configured of, for example, several tens to several hundreds of transducer units 42. The transducer array 41 of the present embodiment has one hundred and twenty-eight transducer units 42. The transducer units 42 are configured by the plurality of transducer elements 33 aligned in the longitudinal direction thereof. In the present modified example, one transducer unit 42 is configured by the sixty-four transducer elements 33 aligned one-dimensionally.

In the transducer array 41 of the present modified example, the transducer element 33 configures the minimum driving unit for transmitting and receiving ultrasonic waves, unlike the above-described embodiment. That is, the transducer unit 42 configured by the one-dimensionally aligned transducer elements 33 configures a one-dimensional ultrasonic transducer array, and by aligning the plurality of transducer units 42, the transducer array 41 as the two-dimensional ultrasonic transducer array is configured.

A plurality of driving circuits 44 which are disposed on the inner circumferential surface of the FPC 35 are electrically connected to the transducer elements 33, respectively. Furthermore, the driving circuits 44 are electrically connected to a plurality of signal electrodes 46 and ground electrodes 47 which are formed on the outer circumferential surface of the cylindrically-shaped FPC 35. Note that the signal electrodes 46 are shown like one electrode in FIG. 10. However, the signal electrodes 46 are divided corresponding to the number of transducer elements 33, and one signal electrode is disposed for one transducer element 33.

The ultrasonic endoscope including the transducer array 41 having the above-described configuration can perform simultaneously or alternately the so-called electronic radial scan to radially transmit and receive ultrasonic waves on the plane substantially perpendicular to the insertion axis of the distal end rigid portion 20, and the so-called electronic sector scan to radially transmit and receive ultrasonic waves on the plane containing the insertion axis of the distal end rigid portion 20. That is, the ultrasonic endoscope of the present modified example can acquire three-dimensional ultrasonic images by performing three-dimensional ultrasonic scan in a body cavity. Furthermore, the ultrasonic endoscope including the transducer array 41 can acquire the three-dimensional ultrasonic images also by performing a three-dimensional ultrasonic scan that carries out in a complex manner, the electronic radial scan and the linear scan that moves the plane on which the radial scan is performed in the direction of insertion axis of the distal end rigid portion 20.

Note that it is needless to say that the present invention includes not only the configuration in which the minimum driving units for transmitting and receiving ultrasonic waves are arranged in an array shape as in the above-described modified example but also a configuration of the ultrasonic transducer in which only one of the minimum driving units is used.

In addition, the ultrasonic diagnostic apparatus of the present embodiment may be an ultrasonic probe not including an optical observation window, or may be a capsule ultrasonic endoscope. The ultrasonic diagnostic apparatus may be a so-called extracorporeal ultrasonic diagnostic apparatus for performing an ultrasonic scan from a body surface of a subject toward a body cavity. In addition, the ultrasonic diagnostic apparatus may be a nondestructive inspection apparatus and a nondestructive flaw detection apparatus used in industrial fields.

Second Embodiment

Figure 10:
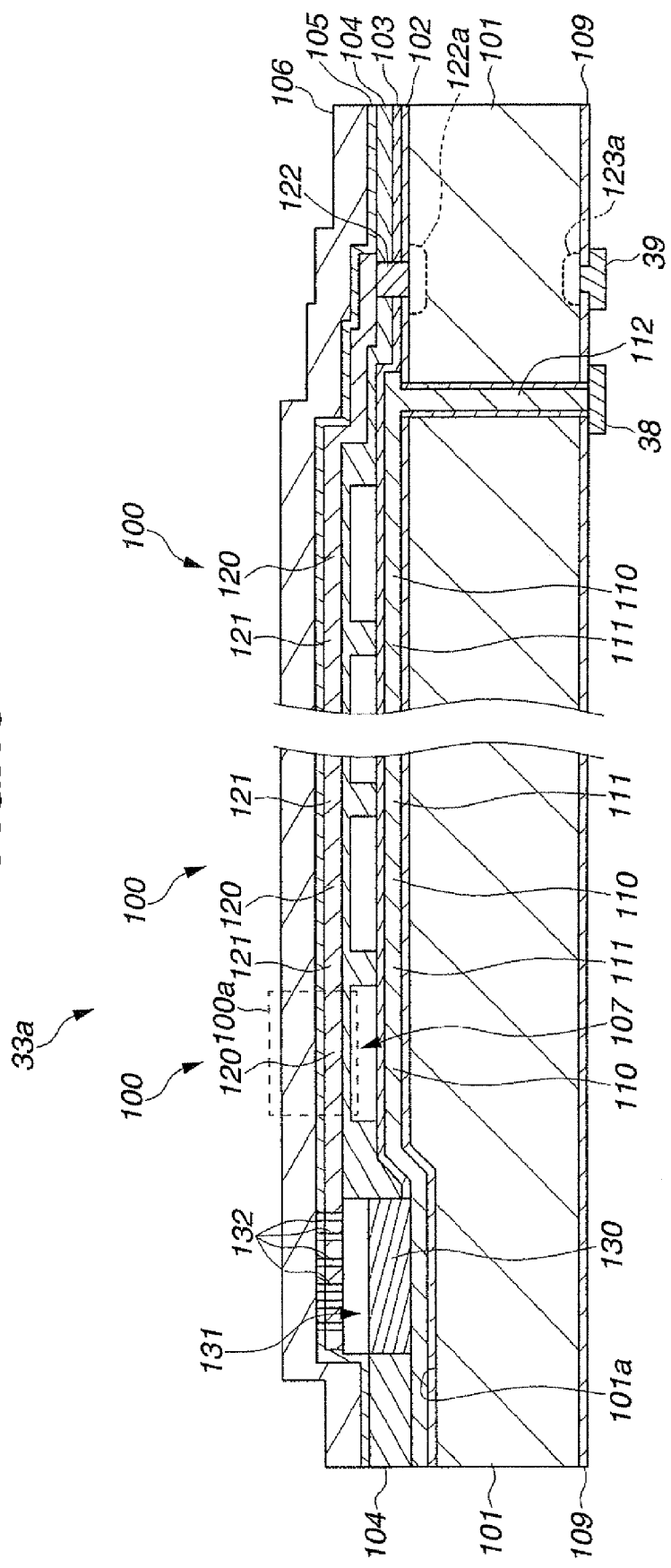
FIG. 10 is a cross-sectional view of a transducer element according to a second embodiment.

Hereinafter, the second embodiment of the present invention is described with reference to FIG. 10. FIG. 10 is a cross-sectional view of the transducer element according to the second embodiment.

The second embodiment differs from the first embodiment only in the configuration of the region where the electret is formed. Therefore, only the different point is described. The same components as those in the first embodiment are attached with the same reference numerals, and the descriptions thereof are appropriately omitted.

Compared with the first embodiment, the transducer element of the present embodiment has a configuration in which the region of a transducer element 33a where the electret 130 is formed does not project from the region where the transducer cells 100 are formed, in the transmitting direction of ultrasonic waves, as shown in FIG. 10.

The transducer element 33a of the present embodiment eliminates the irregularity of the surface on the transmitting side of ultrasonic waves by forming a recessed portion 101a in the region on the silicon substrate 101 where the electret 130 is formed.

With such a configuration, the patterning accuracy in the semiconductor process of forming the transducer cells 100 is improved in the transducer unit as the ultrasonic transducer of the present embodiment.

That is, the transducer element of the present embodiment can improve the accuracy of the dimension of the transducer cells 100 compared with the first embodiment, thereby enabling the transducer cells 100 having uniform acoustic characteristics to be formed.

Third Embodiment

Figure 11:
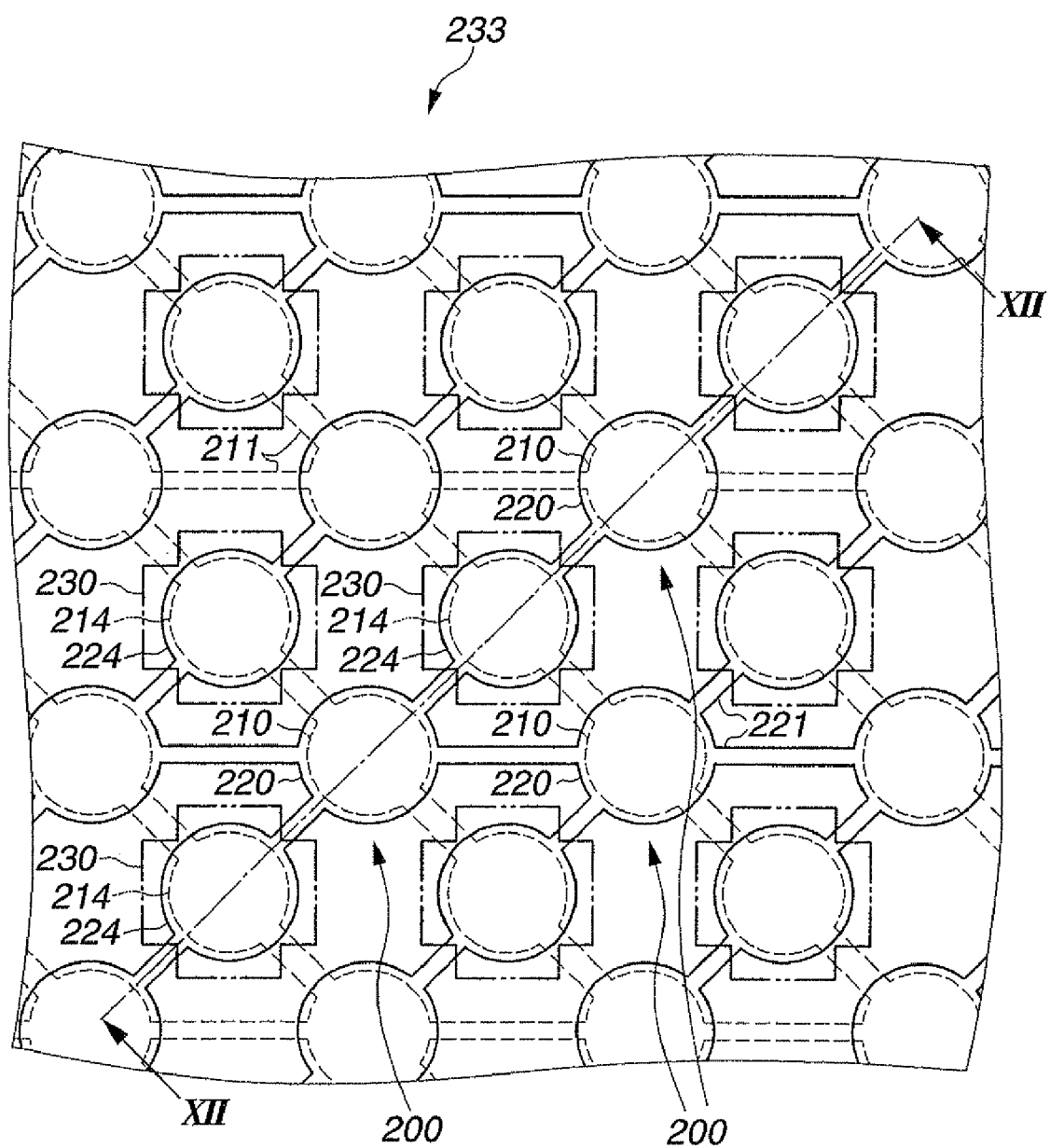
FIG. 11 is a top view of a transducer element according to a third embodiment.
Figure 12:
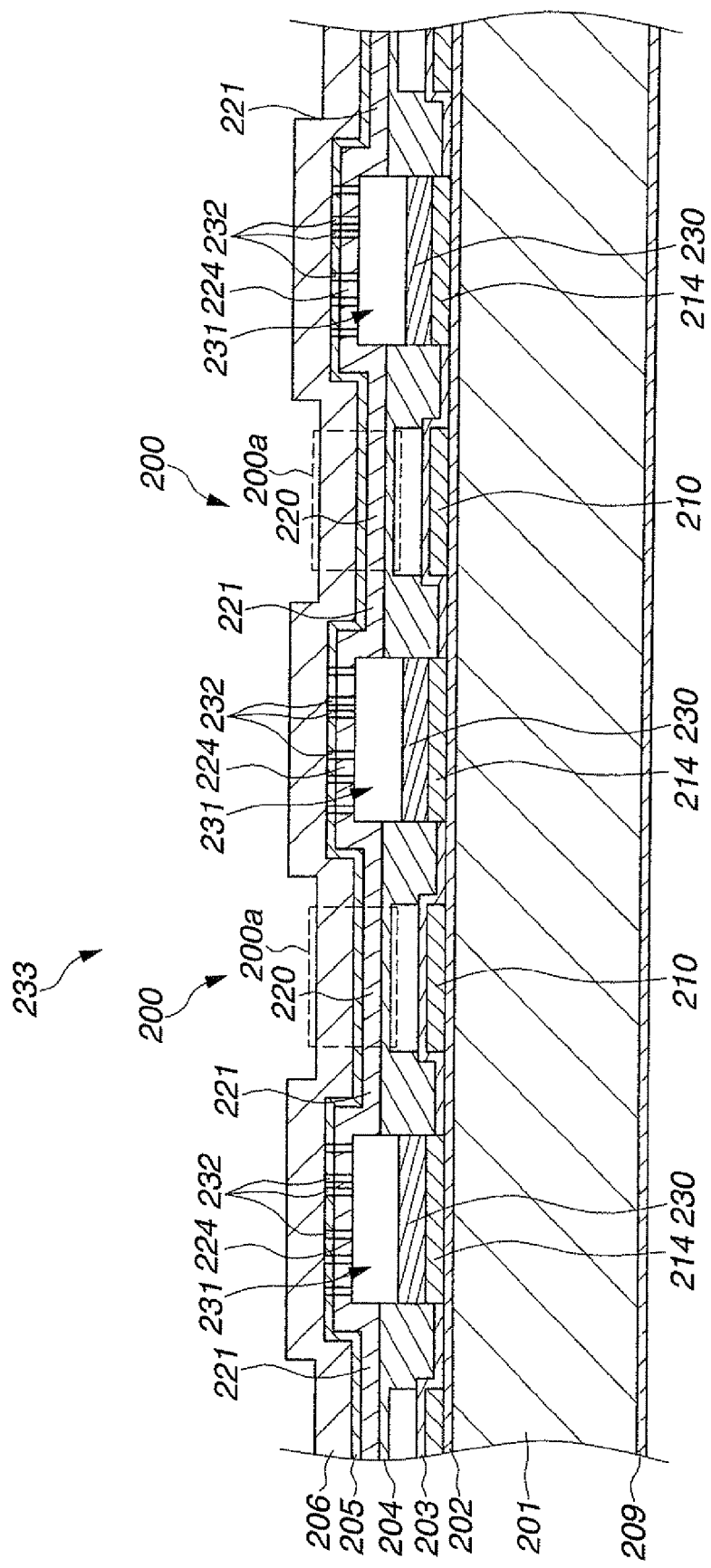
FIG. 12 is a cross-sectional view along the XII-XII line in FIG. 11.

Hereinafter, the third embodiment of the present invention is described with reference to FIGS. 11 and 12. FIG. 11 is a top view of an ultrasonic transducer element 233 of the present embodiment. FIG. 12 is a cross-sectional view along the XII-XII line in FIG. 11.

The third embodiment is different from the first embodiment only in the positional relationship between the region where the transducer cells are formed and the region where the electrets are formed. Therefore, only the different point is described below. The same components as those in the first embodiment attached with the same reference numerals and description thereof appropriately omitted.

As shown in FIG. 11, the transducer element 233 of the present embodiment is configured by including a plurality of transducer cells 200 aligned in rows and columns when viewed from above (transmitting direction of ultrasonic waves) and a plurality of electrets 230 formed in a region separated from the transducer cells 200 when viewed from above. In FIG. 11, for convenience of description, patterns formed by the same conductive layer as upper electrodes 220 of the transducer cells 200 are shown by solid lines, patterns formed by the same conductive layer as lower electrodes 210 are shown by dashed lines, and regions where the electrets 230 are disposed are shown by two-dot chain lines.

Specifically, when focusing on the transducer cells 200 at four places aligned adjacently one another in two rows and columns, which are a part of the transducer element 233, the electret 230 is disposed at a position of equal distance from all of the transducer cells 200 at the four places, in the direction perpendicular to the transmitting direction of ultrasonic waves. That is, on the cross section (FIG. 12) cut by the plane which contains a center of the transducer cells 200 at two places positioned at opposing corners of the transducer cells 200 at the four places in two rows and two columns and is parallel to the transmitting direction of ultrasonic waves, the region where the transducer cells 200 are disposed and the region where the electrets 230 are disposed are alternately aligned.

As shown in FIG. 12, as in the first embodiment, the transducer element 233 of the present embodiment is formed, by the micromachining technology using a semiconductor process and the like, on a silicon substrate 201 configured of a low-resistance silicon semiconductors, which includes on both surfaces thereof a first insulating film 202 and a rear surface insulating film 209 that are silicon oxide films having electric insulation.

Since the configurations of the transducer cells 200 and the region where the electrets 230 are disposed are the same as those in the first embodiment, the detailed descriptions thereof are omitted and only the configurations thereof are described below.

The transducer cell 200 is configured by including the lower electrode 210 as a substantially circular-shaped conductive layer when viewed from above, the upper electrode 220 as a substantially circular-shaped conductive layer when viewed from above, which is disposed so as to face the lower electrode, and a cavity 207 as a substantially cylindrically-shaped air gap portion interposed between the lower electrode 210 and the upper electrode 220. For the purpose of electrically insulating the lower electrode 210 and the upper electrode 220, a second insulating film 203 and a third insulating film 204 are disposed respectively on the cavity 207 sides of the lower electrode 210 and the upper electrode 220. In addition, a protective film 205 and a paraxylylene resin film 206 are disposed on the upper electrode 220.

The transducer cell 200 of the present embodiment transmits and receives ultrasonic waves by vibration of a membrane 200a (vibration membrane) which is a film-like structure with elasticity configured of the upper electrode 220 of the above-described transducer cell 200, the third insulating film 204, the protective film 205, and paraxylylene resin film 206.

On the other hand, the region where the electret 230 is disposed is configured of a lower conductive layer 214 electrically connected to the lower electrode 210 of the transducer cell 200, an upper conductive layer 224 electrically connected to the upper electrode 220, and the electret 230 interposed between the lower conductive layer 214 and the upper conductive layer 224. In addition, an air gap portion 231 as an insulating layer is interposed between the electret 230 and the upper conductive layer 224.

Furthermore, in the upper conductive layer 224 and the protective film 205 that are disposed above the electret 230 are drilled a myriad of microscopic through holes 232 penetrating the upper conductive layer 224 and the protective film 205 in a thickness direction.

In addition, as shown in FIG. 11, in the present embodiment, in regions other than the regions where the transducer cells 200 and the electrets 230 are disposed, the patterns Conned by the same conductive layer as the upper electrode 220 (the solid lines in FIG. 11) and the patterns formed by the same conductive layer as the lower electrode 210 (the dashed lines in FIG. 11) are disposed so as not to overlap with each other.

That is, in the present embodiment, an upper electrode wiring 221 electrically connecting the plurality of upper electrodes 220 and the plurality of upper conductive layers 224 and a lower electrode wiring 211 electrically connecting the plurality of lower electrodes 210 and the plurality of lower conductive layers 214 are disposed alternately or at different angles in regions different from each other when viewed from above.

Thus, by disposing the upper conductive layers 224 and the lower conductive layers 214 so as not to overlap with each other when viewed from above, generation of a parasitic capacitance is prevented in the wiring portions.

The transducer element 233 having the above-described configuration further includes the effects below in addition to the effects same as those in the first embodiment.

In the transducer unit of the present embodiment, by disposing the electrets 230 between the plurality of transducer cells 200, when viewing the transducer elements from the transmitting direction of ultrasonic waves, the area of the region not contributing to the transmission and reception of ultrasonic waves can be made smaller than that in the first embodiment. That is to say, utilization efficiency of the ultrasonic waves transmitting/receiving surfaces of the transducer element can be improved.

Therefore, the transducer element of the present embodiment is capable of providing a smaller-sized ultrasonic diagnostic apparatus which can transmit and receive ultrasonic waves with higher efficiency.

Note that, the electrets 230 would suffice to retain an amount of charge sufficient to apply direct current voltage to the transducer cells 200 of the transducer element, and the electrets 230 do not have to be disposed in all the regions between the plurality of transducer cells 200, as shown in FIG. 11.

In addition, though the electrets are disposed dividedly in a plurality of regions in the above-described present embodiment, the electrets may be disposed in a single continuous shape as long as the electrets are disposed in a separated region which is different from the region where the transducer cells are formed.

Figure 13:
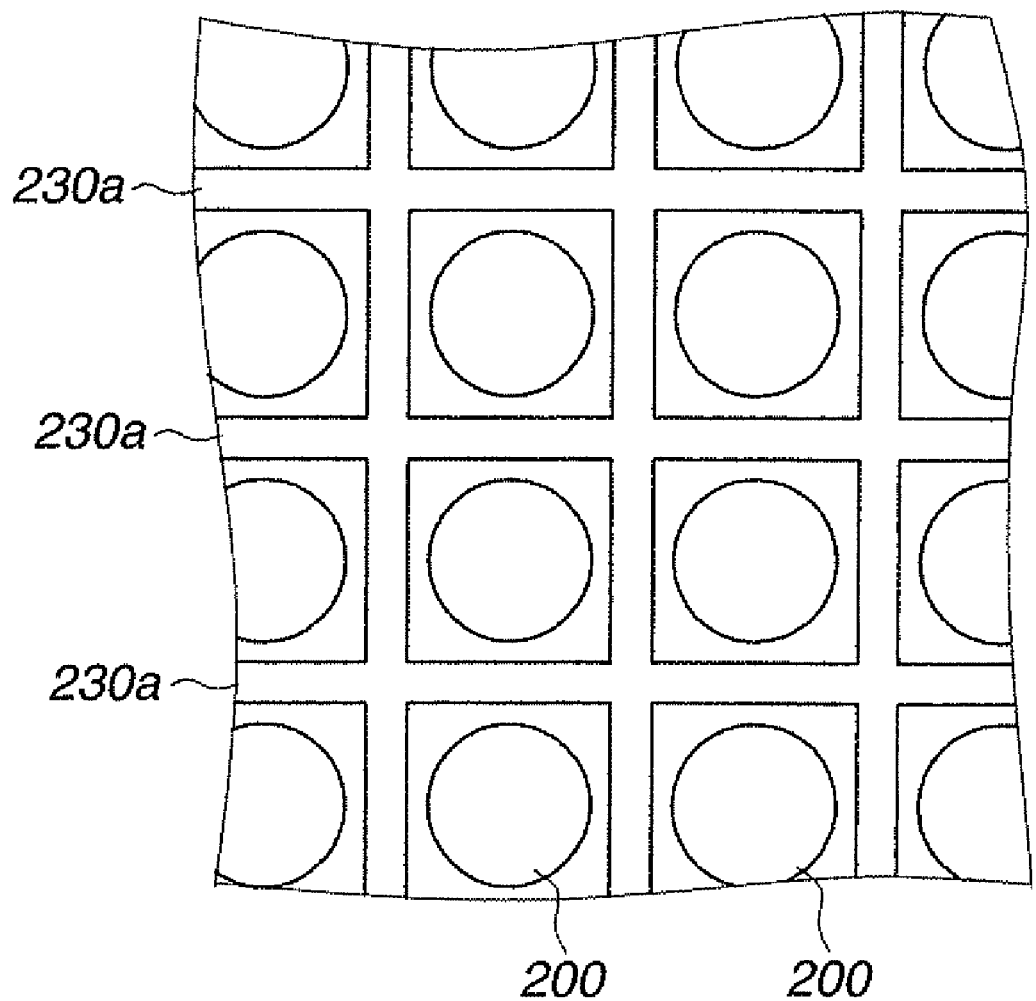
FIG. 13 is a top view of a transducer element according to a modified example of the third embodiment.

For example, as shown in FIG. 13, electrets 230a may be disposed in a lattice-shaped region to fill in the regions between the plurality of transducer cells 200 aligned in rows and columns.

Fourth Embodiment

Figure 14:
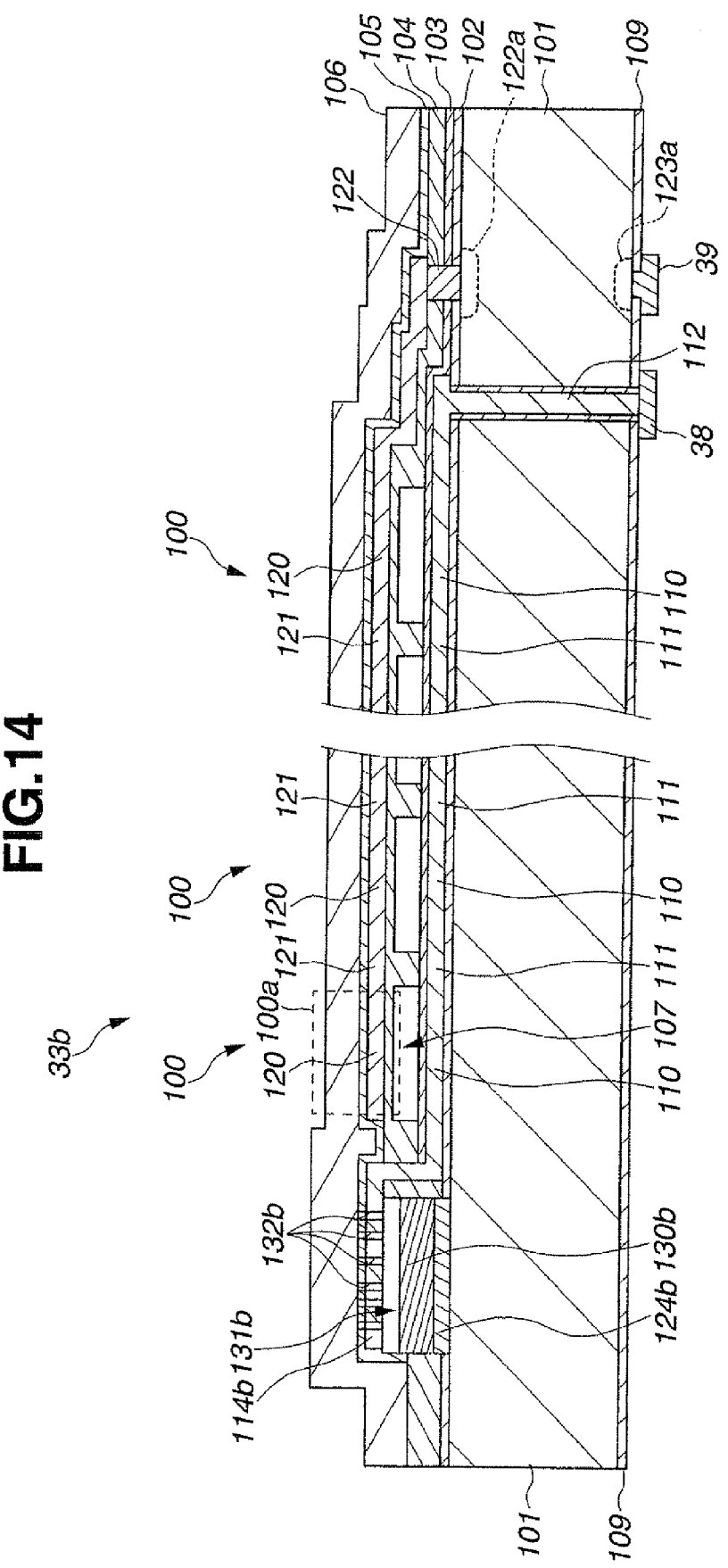
FIG. 14 is a cross-sectional view of a transducer element according to a fourth embodiment.

Hereinafter, the fourth embodiment of the present invention is described with reference to FIG. 14. FIG. 14 is a cross-sectional view of the transducer element according to the fourth embodiment.

The fourth embodiment is different from the first embodiment in the configuration of the region where the electrets are formed. Therefore, only the different point is described. The same components as those in the first embodiment are attached with the same reference numerals, and the descriptions thereof are appropriately omitted.

As shown in FIG. 14, in the transducer element of the present embodiment, compared with that in the first embodiment, a first conductive layer 114b electrically connected to the lower electrode 110 of the transducer cell 100 is disposed above an electret 130b, and a third conductive layer 124b having the same electrical potential as that of the upper electrode 120 of the transducer cell 100 is disposed beneath the electret 130b, in the region of the transducer element 33b where the electret 130b is formed.

More specifically, between the electret 130b and the silicon substrate 101 as a ground potential is disposed the third conductive layer 124b electrically connected to the silicon substrate. In addition, the first conductive layer 114b is disposed above the electret 130b in a facing manner, through the air gap portion 131.

The first conductive layer 114b, which is disposed above the electret 130b, is provided with a myriad of through holes 132b drilled so as to penetrate the first conductive layer 114b in the thickness direction, in a region overlapping with the electret 130b when viewed from above, that is, in the ultrasonic wave transmitting direction.

As in the first embodiment, the charging processing on the electret 130b of the present embodiment is performed through the through holes 132b after the first conductive layer 114b has been formed above the electret 130b. That is, even if the first conductive layer 114b electrically connected to the lower electrode 110 is formed above the electret 130b as in the present embodiment, the same effects as those in the first embodiment can be obtained.

Fifth Embodiment

Figure 15:
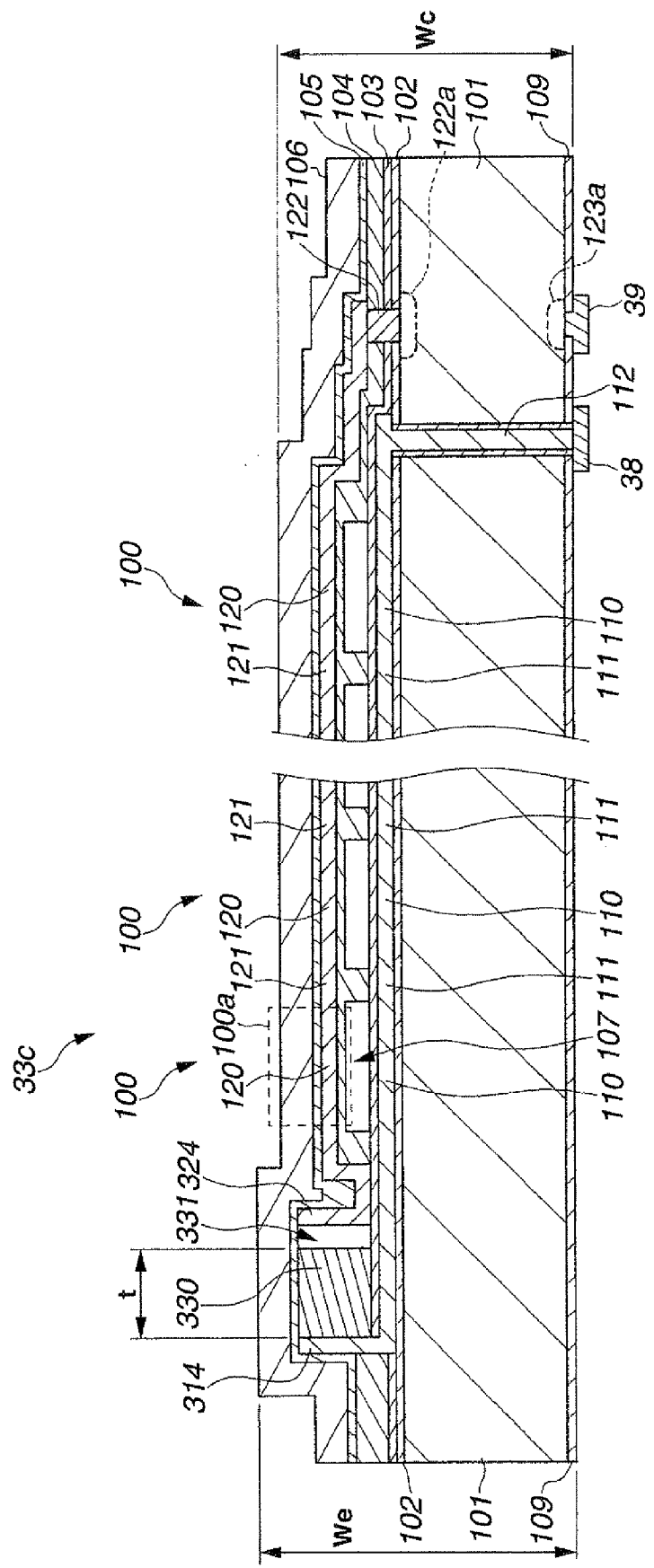
FIG. 15 is a cross-sectional view of a transducer element according to a fifth embodiment.

Hereinafter, the fifth embodiment of the present invention is described with reference to FIG. 15. FIG. 15 is a cross-sectional view of the transducer element according to the fifth embodiment.

The fifth embodiment is different from the first embodiment only in the configuration of the region where the electret is formed. Therefore, only the different point is described. The same components as those in the first embodiment are attached with the same reference numerals, and the descriptions thereof are appropriately omitted.

Specifically, an electret 330 of the present embodiment is interposed between a first conductive layer 314 electrically connected to the lower electrode 110 of the transducer cell 100 and a second conductive layer 324 electrically connected to the upper electrode 120.

Here, in the present embodiment, the first conductive layer 314 and the second conductive layer 324 are plate-shaped electrodes disposed facing in parallel to each other, and the surfaces facing each other are disposed so as to be substantially parallel to the normal line direction of the surface of the silicon substrate 101. That is, the first conductive layer 314 and the second conductive layer 324 respectively have plane portions substantially parallel to the transmitting direction of the ultrasonic waves of the transducer element 33c, and are disposed such that the plane portions face each other.

Therefore, the electret 330 of the present embodiment is held between the first conductive layer 314 and the second conductive layer 324 in a direction substantially parallel to the surface of the silicon substrate 101, that is, the direction substantially perpendicular to the transmitting direction of ultrasonic waves.

That is, the electret 330 of the present embodiment applies a potential difference between the lower electrode 110 and the upper electrode 120 of the transducer cell 100, as described above, the direction of the electrical field generated by the electret 330 is substantially perpendicular to the transmitting direction of ultrasonic waves of the transducer cell 100, that is, the layer direction of the lower electrode 110 and the upper electrode 120.

In yet other words, the electret 330 interposed between the first conductive layer 314 and the second conductive layer 324 is disposed such that at least a part thereof is exposed more externally than the first conductive layer 314 and the second conductive layer 324, in the transmitting direction of ultrasonic waves of the transducer element 33c, that is, in the layer direction of the lower electrode 110 and the upper electrode 120 as the pair of electrodes of the transducer cell 100.

In addition, an air gap portion 331 as an insulating layer is interposed between the electret 330 and the second conductive layer 324. In the present embodiment, the air gap portion 331 is formed by the sacrificial layer etching as a known technology. Note that the air gap portion 331 may be other insulating films, for example, a silicon oxide film, silicon nitride film and the like, as long as the film electrically insulates the electret 330 and the second conductive layer 324.

The protective film 105 having electrical insulation is formed on the first conductive layer 314, the second conductive layer 324, the electret 330, and the air gap portion 331. In addition, the paraxylylene resin film 106 is formed on the protective film 105.

In addition, as shown in FIG. 15, in the transducer element 33c, the region where the electret 330 is disposed is formed so as to project upward (in the transmitting direction of ultrasonic waves) more than the region where the transducer cells 100 is formed. Specifically, in the transducer element 33c, the thickness We of the region where the electret 330 is disposed becomes larger than the thickness We of the region where the transducer cells 100 are formed.

Thus, with the configuration in which the region adjacent to the transducer cells 100 projects in the transmitting direction of ultrasonic waves more than the region where the transducer cells 100 are formed, the transducer element 33 of the present embodiment can prevent destruction of the membranes 100a of the transducer cells 100 resulting from a contact with other objects, as in the first embodiment.

In the transducer element 33c as the ultrasonic transducer of the present embodiment having the above-described configuration, the charging processing on the electret 330 by the corona discharge is performed after completion of the processes of forming the transducer cells 100 part and the region where the electret 330 is disposed using the semiconductor process.

That is, the charging processing on the electret 330 by the corona discharge is performed through the protective film 105 after the protective film 105 has been formed. Then, after the charging processing has been performed on the electret 330, the paraxylylene resin film 106 is formed by the spin coat method or the like, thereby completing the structure of the cell forming surface side of the transducer element 33c.

Below, description is made on the effects of the ultrasonic transducer and the ultrasonic diagnostic apparatus of the present embodiment that have the above-described configuration.

In the transducer element 33c of the present embodiment, when viewed from the transmitting direction of ultrasonic waves, that is, the layer direction of the lower electrode 110 and the upper electrode 120 as the pair of the electrodes of the transducer cell 100, the electret 330 is disposed in a region not overlapping with and separated from the transducer cell 100. Therefore, in the transducer element 33c of the present embodiment, the thickness of the electret 330 and the distance between the lower electrode 110 and the upper electrode 120 can be set independently.

Therefore, compared with a conventional capacitive ultrasonic transducer including an electret disposed between a pair of parallel plate electrodes, in the transducer element 33c of the present embodiment, the distance (gap) between the pair of parallel plate electrodes (the lower electrode 110 and the upper electrode 120 in the present embodiment) can be made smaller and the electret 330 as the charge retention means can be made thicker.

Accordingly, with the present embodiment, the distance between the lower electrode 110 and the upper electrode 120 is made smaller than in the conventional transducer to increase the capacitance between the electrodes, which can improve the sound pressure of the transmitted ultrasonic waves and the sensitivity to the received ultrasonic waves and make the electret 330 to have a thickness to allow permanent and stable charge retention.

In addition, the transducer element 33c of the present embodiment can be configured to be thinner than the conventional capacitive ultrasonic transducer, since the lower electrode 110 and the upper electrode 120, and the electret 330 are not disposed in a layered manner in the thickness direction.

In addition, in the present embodiment, the electret 330 is held in the direction substantially parallel to the surface of the silicon substrate 101, that is, in the direction substantially perpendicular to the transmitting direction of ultrasonic waves. Therefore, the thickness of the electret 330 is defined, as shown by the reference symbol t in FIG. 15, by the dimension of the electret 330 in the direction in which the electret 330 is held between the first conductive layer 314 and the second conductive layer 324.

That is, in the present embodiment, the thickness t of the electret 330 can be set independently of the thickness of the transducer element 33c in the transmitting direction of ultrasonic waves. Therefore, with the present embodiment, the transducer element 33c can be formed to be thinner in the transmitting direction of ultrasonic waves.

Furthermore, compared also with a conventional capacitive ultrasonic transducer in which a transducer cell and an electret are layered in the thickness direction instead of disposing the electret between a pair of the electrodes, the transducer element 33c of the present embodiment can be made thinner in the transmitting direction of ultrasonic waves.

Therefore, the transducer element 33c as the ultrasonic transducer of the present embodiment is thinner and has a higher sound pressure of the transmitted ultrasonic waves and a higher sensitivity to the received ultrasonic waves than the conventional one, and in addition, can permanently maintain the characteristics.

In other words, at the time of exerting a predetermined sound pressure of the transmitted ultrasonic waves and sensitivity to the received ultrasonic waves, the present embodiment realizes an ultrasonic transducer which maintains the initial performance over a long period of time, and is thinner and can be driven at lower voltage compared with the conventional ones.

In addition, the present embodiment enables the ultrasonic diagnostic apparatus including the transducer element 33c which is thin and can be driven at a low voltage to have a longer operation life and a reduced size than the conventional one. For example, with the ultrasonic endoscope 1 shown in FIG. 1, the outer diameter of the transducer array 31 can be made smaller than the conventional ones, which realizes a diagnosis at low burden for the patient.

In addition, in the transducer element 33c of the present embodiment, the electret 330 is disposed such that at least a part thereof is exposed in the transmitting direction of ultrasonic waves of the transducer element 33c relative to the first conductive layer 314 and the second conductive layer 324, and only the protective film 105 and the paraxylylene resin film 106 are formed on the region where the electret 330 is exposed. Note that it is preferable that the paraxylylene resin includes fluorine (F), since its chemical resistance is high.

In the transducer element 33c of the present embodiment having such a configuration, the process of performing the charging processing on the electret 130 by the corona discharge can be easily performed after the protective film 105 has been formed. In other words, in the present embodiment, after all the layer structures to be formed by the semiconductor process have been formed, the charging processing is performed on the electret 330. After the charging processing has been performed on the electret 330, a process of heating the electret 330 up to a high temperature, for example the process like the CVD, does not exist.

Generally, the electret as the charge retention means has such a property that the charge is discharged and the retaining charge amount decreases when the electret temperature is increased. For example, in the electret 330 of the present embodiment which is made of the silicon oxide film, when the temperature thereof is increased to about not less than 400 degrees Celsius, decrease in charging amount occurs. Since decrease in the charging amount retained by the electret 330 leads to decrease in direct-current voltage components to be applied between the lower electrode 110 and the upper electrode 120, the sensitivity to the received ultrasonic waves of the element 33c decreases in particular.

However, with the present embodiment, as in the first embodiment, the transducer element 33c can be manufactured without heating the electret 330 subjected to the charging processing up to a temperature at which the charge amount retained by the electret 330 decreases.

Therefore, the transducer element 33c, as the ultrasonic transducer of the present embodiment, allows the charge amount retained by the electret 330 to be higher, and has a higher sensitivity to the received ultrasonic waves when driven at a low voltage, compared with conventional transducers.

Furthermore, since the transducer element 33c of the present embodiment does not require the semiconductor process performed at a relatively lower temperature, for example, at a processing temperature not more than 400 degrees Celsius, the transducer element 33c can be manufactured at low cost by a more universal semiconductor manufacturing apparatus.

Furthermore, in the forming process of the transducer element 33c of the present embodiment, unlike the first embodiment, the charging processing on the electret 330 by the corona discharge is performed in a state where the conductive layer does not exist on the upper layer side of the electret 330. Therefore, compared with the first embodiment, the charge to be injected into the electret 330 does not leak out through the conductive layer at the time of the charging processing in the present embodiment, which enables the charging processing to be more effectively performed on the electret.

Note that in the above-described present embodiment, though it is described that the electret 330 is formed by performing the charging processing on the single-layer or multi-layer inorganic film such as a silicon oxide film, the configuration of the electret 330 is not limited to this.

For example, the electret 330 may be made of an organic film, and particularly, may be formed by charging the fluorocarbon resin, which is generally called as FEP, by the corona discharge, or configured of another organic film such as of fluorocarbon resin other than FEP, polyimide, polypropylene, polymethylpentene, and the like.

The electrets made of these organic films have been conventionally used in other fields and known to be able to stably retain the charge over a long period of time. However, the electrets made of the organic films have such a property that the retaining charge amount decreases when heated to a high temperature, and in particular, the decrease in the retaining charge amount occurs at about 100 to 200 degrees Celsius which is lower than in the case of the electrets made of inorganic films. Therefore, it has been difficult to apply the electrets made of organic film to the capacitive ultrasonic transducer formed by the semiconductor process.

However, in the transducer element 33c of the present embodiment, since the charging processing is performed on the electret after completion of the semiconductor process as described above, even if the electret is configured of an organic film, the charge amount retained by the electret is not decreased.

Therefore, with the present embodiment, the electret of the transducer element 33c can be configured of the organic film capable of stably retaining the charge over a longer period of time than in prior arts, which can provide a capacitive ultrasonic transducer having longer operation life than in prior arts.

In addition, in the above-described present embodiment, the electret 330 retaining negative charge is formed so as to contact the first lower conductive layer 314 electrically connected to the lower electrode 110 of the transducer cell 100. In addition, an air gap portion 331 as an insulating layer is interposed between the electret 330 and the second conductive layer 324.

Such a configuration is effective in a case where the voltage signal outputted from the driving circuit 34 to be applied to the lower electrode 110 at the time of transmitting the ultrasonic waves by the transducer element 33c has a negative polarity. This is because such a configuration allows the direct-current voltage components of the negative polarity to be applied between the lower electrode 110 and the upper electrode 120 by the electret 330, which can prevent the charge retained by the electret 330 from flowing out from the upper conductive layer 324 as the ground potential.

In addition, in order to more certainly ensure the charge retention by the electret 330, it is effective to cover the entire surface of the periphery of the electret 330 with an insulating film. Note that it is needless to say that the insulating film covering the entire surface of the periphery of the electret 330 may be divided into a plurality of insulating films.

Figure 16:
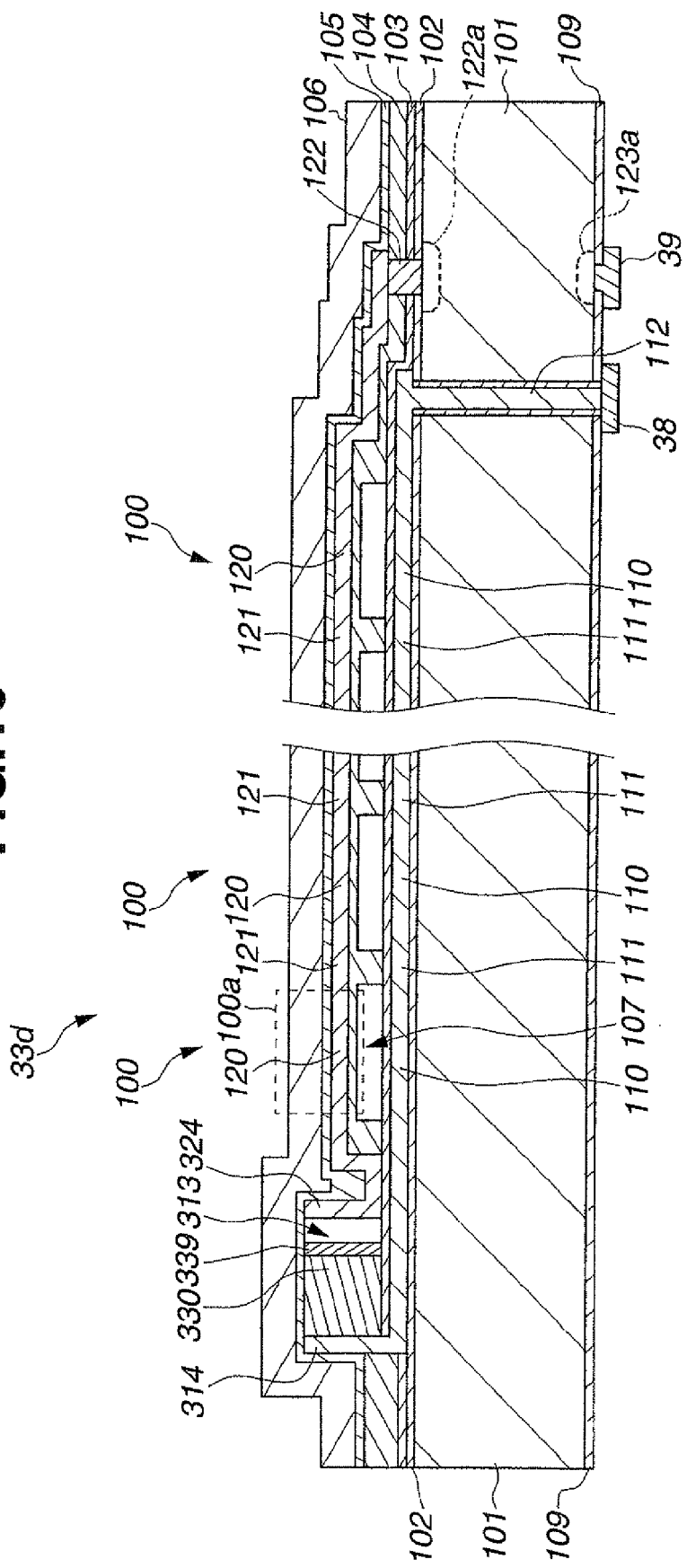
FIG. 16 is a cross-sectional view of a transducer element according to a modified example of the fifth embodiment.

For example, as shown in FIG. 16 as a modified example of the present embodiment, if the electret 330 is configured such that the periphery thereof is covered by an insulating film by forming an insulating layer 339 between the electret 330 and the air gap portion 331, the charge retention by the electret 330 can be more ensured. In the modified example of the present embodiment shown in FIG. 16, when the electret 330 is configured of a silicon oxide film, it is preferable that the second insulating film 104, the protective film 105, the insulating layer 339 which cover the electret 330 are made of a silicon nitride film.

Sixth Embodiment

Figure 17:
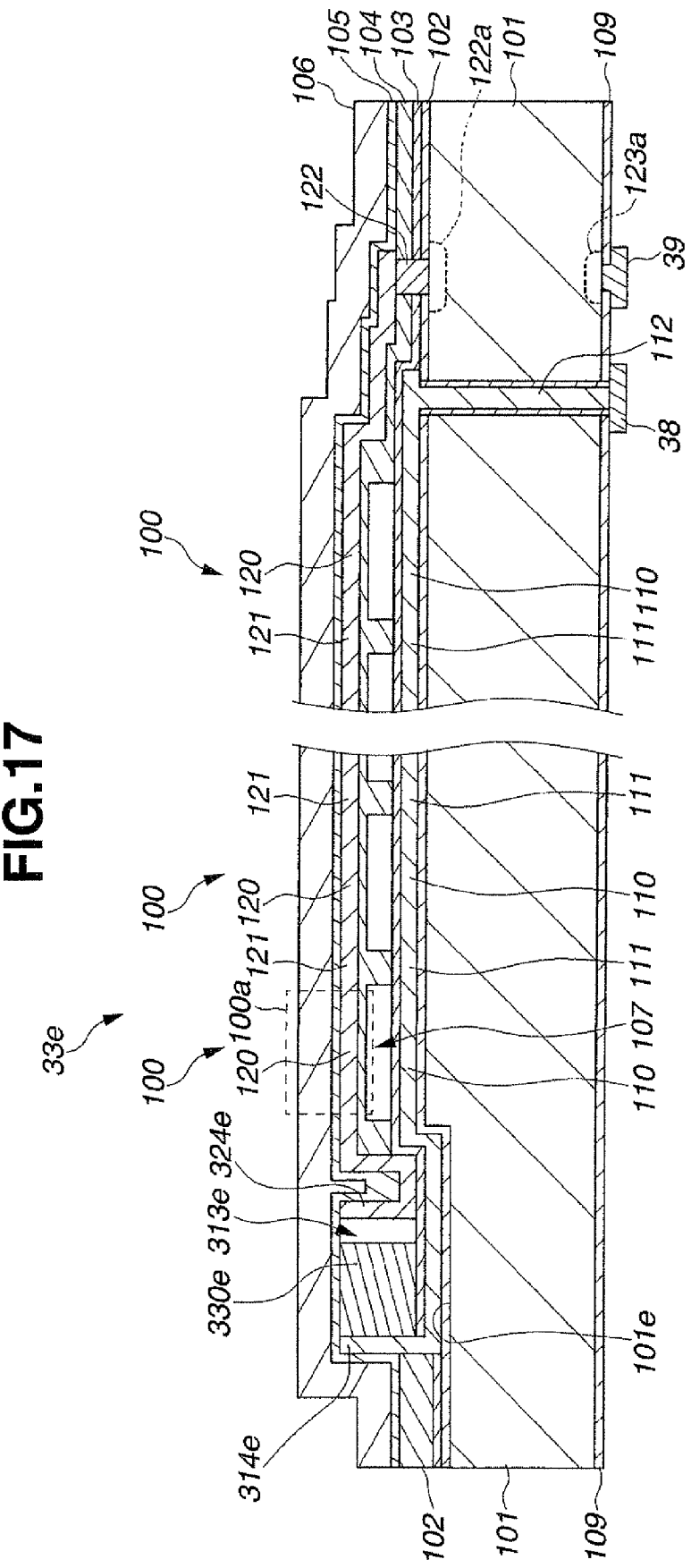
FIG. 17 is a cross-sectional view of a transducer element according to a sixth embodiment.

Hereinafter, the sixth embodiment of the present invention is described with reference to FIG. 17. FIG. 17 is a cross-sectional view of the transducer element according to the sixth embodiment.

The sixth embodiment is different from the fifth embodiment only in the configuration of the region where the electret is formed. Therefore, only the different point is described. The same components as those in the fifth embodiment are attached with the same reference numerals, and the descriptions thereof are appropriately omitted.

Compared with the transducer element in the fifth embodiment, the transducer element of the present embodiment has a configuration in which the region of a transducer element 33e where an electret 330e is formed does not project in the transmitting direction of ultrasonic waves from the region where the transducer cells 100 are formed, as shown in FIG. 17.

The transducer element 33e of the present embodiment eliminates the irregularity on the surface on the ultrasonic waves transmitting side by forming a recess portion 101e in the region on the silicon substrate 101 where the electret 330e is formed.

With such a configuration, the patterning accuracy in the semiconductor process of forming the transducer cells 100 is improved in the transducer element 33e as the ultrasonic transducer of the present embodiment.

That is, the transducer element 33e of the present embodiment can improve the accuracy of the dimensions of the transducer cells 100 compared with the fifth embodiment, thereby enabling the transducer cells 100 having uniform acoustic characteristics to be formed.

Seventh Embodiment

Figure 18:
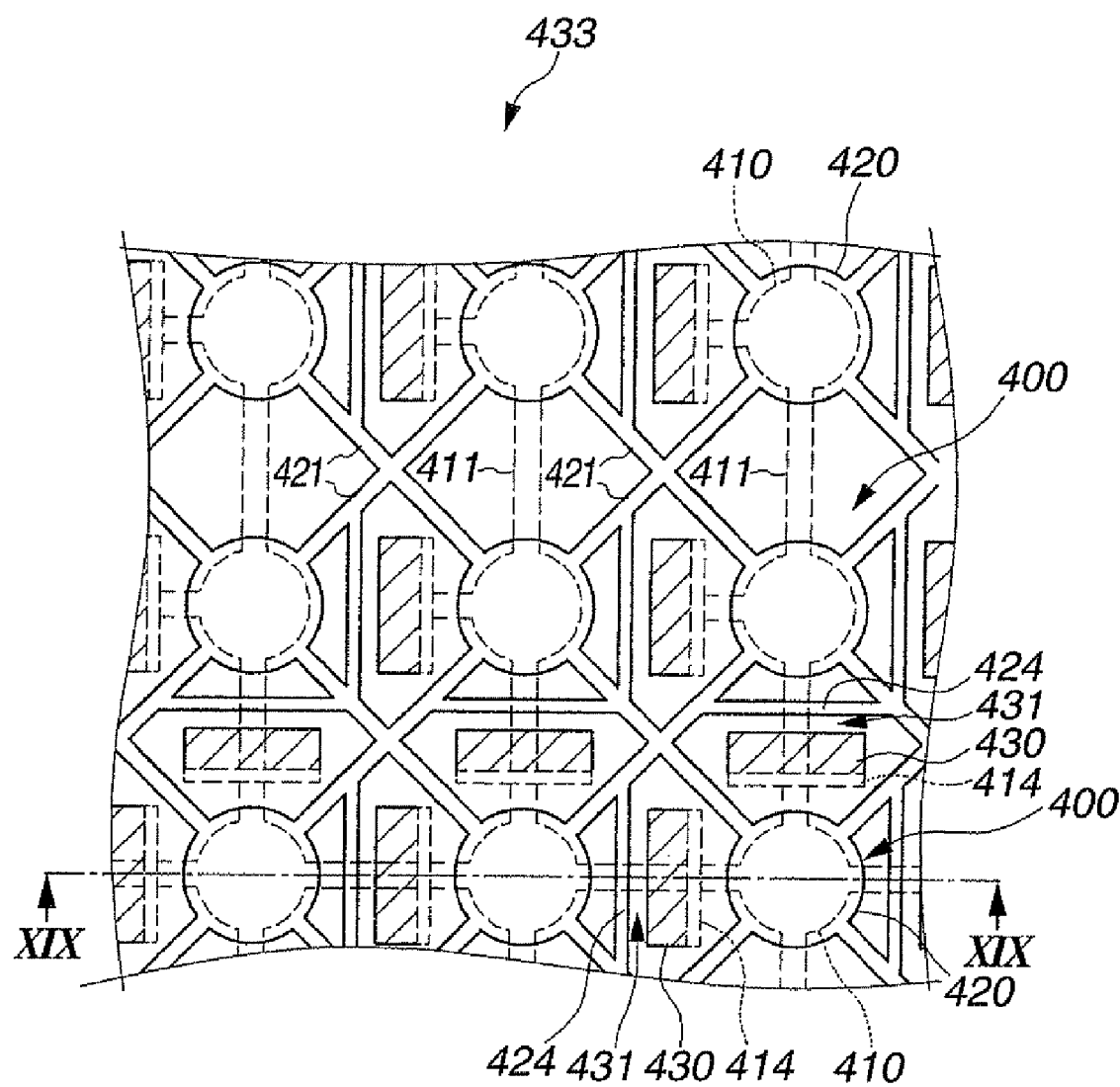
FIG. 18 is a top view of a transducer element according to a seventh embodiment.
Figure 19:
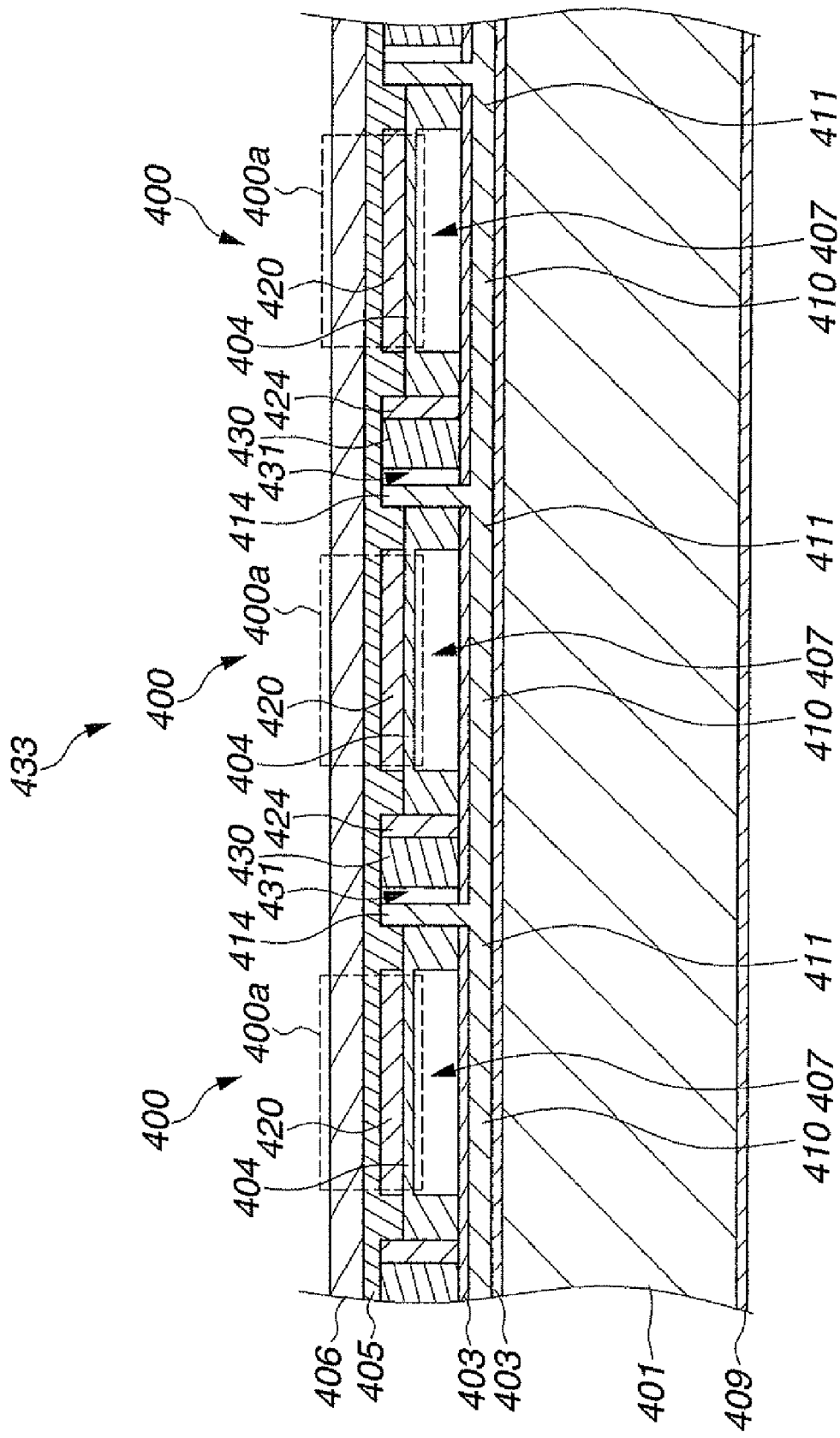
FIG. 19 is a cross-sectional view along the XIX-XIX line in FIG. 18.

Hereinafter, the seventh embodiment of the present invention is described with reference to FIGS. 18 and 19. FIG. 18 is a top view of an ultrasonic transducer element 433 of the present embodiment. FIG. 19 is a cross-sectional view along the XIX-XIX line in FIG. 18.

The seventh embodiment is different from the fifth embodiment only in the positional relationship between the region where the transducer cells are formed and the region where the electrets are formed. Therefore, only the different point is described. The same components as those in the fifth embodiment are attached with the same reference numerals, and the descriptions thereof are appropriately omitted.

As shown in FIG. 18, the transducer element 433 of the present embodiment is configured by including a plurality of transducer cells 400 aligned in rows and columns when viewed from above (transmitting direction of ultrasonic waves) and a plurality of electrets 430 formed in a region separated from the transducer cells when viewed from above. As shown in FIG. 18 for convenience of description, patterns formed by the same conductive layer as upper electrodes 420 of the transducer cells 400 are shown by solid lines, patterns formed by the same conductive layer as lower electrodes 410 are shown by dashed lines, and regions where the electrets 430 are disposed are shown by two-dot chain lines.

The electrets 430 are disposed in the respective regions between the plurality of transducer cells 400 aligned in rows and columns. For example, in the present embodiment, the electrets 430 are disposed between the respective transducer cells 400 aligned in the line direction. That is, on the cross section (FIG. 19) cut by the plane containing the center of the plurality of transducer cells 400 aligned in the same row and parallel to the transmitting direction of ultrasonic waves, the region where the transducer cells 400 are disposed and the region where the electrets 430 are disposed are alternately aligned.

As shown in FIG. 19, as in the fifth embodiment, the transducer element 433 of the present embodiment is formed by the micromachining technology using a semiconductor process and the like on a silicon substrate 401 configured of a low-resistance silicon semiconductors, which includes on both surfaces thereof a first insulating film 402 and a rear surface insulating film 409 that are silicon oxide films having electric insulation.

Since the configurations of the regions where the transducer cells 400 and the electrets 430 are disposed are the same as those in the fifth embodiment, the detailed descriptions thereof are omitted and only the configuration thereof is described below.

The transducer cell 400 is configured by including the lower electrode 410 as a substantially circular-shaped conductive layer when viewed from above, the upper electrode 420 as a substantially circular-shaped conductive layer when viewed from above, which is disposed so as to face the lower electrode, and a cavity 407 as a substantially cylindrically-shaped air gap portion interposed between the lower electrode 410 and the upper electrode 420. For the purpose of electrically insulating the lower electrode 410 and the upper electrode 420, a second insulating film 403 and a third insulating film 404 are disposed respectively on the cavity 407 sides of the lower electrode 410 and the upper electrode 420. In addition, a protective film 405 and a paraxylylene resin film 406 are disposed on the upper electrode 420.

The transducer cell 400 of the present embodiment transmits and receives ultrasonic waves by vibration of a membrane 400a (vibration membrane) which is a film-like structure with elasticity configured of the upper electrode 420 of the above-described transducer cell 400, the third insulating film 404, the protective film 405, and paraxylylene resin film 406.

On the other hand, the region where the electret 430 is disposed is configured of the first conductive layer 414 electrically connected to the lower electrode 410 of the transducer cell 400, the second conductive layer 424 electrically connected to the upper electrode 420, and the electret 430 interposed between the first conductive layer 414 and the second conductive layer 424. In addition, an air gap portion 431 as an insulating layer is interposed between the electret 430 and the second conductive layer 424.

The electret 430 is held between the first conductive layer 414 and the second conductive layer 424 in a direction substantially parallel to the surface of the silicon substrate 401, that is, the direction substantially perpendicular to the transmitting direction of ultrasonic waves.

In other words, the electret 430 interposed between the first conductive layer 414 and the second conductive layer 424 is disposed such that at least a part thereof is exposed more externally than the first conductive layer 414 and the second conductive layer 424, in the transmitting direction of ultrasonic waves of the transducer element 433, that is, in the layer direction of the lower electrode 410 and the upper electrode 420 as the pair of electrodes of the transducer cell 400.

In addition, as shown in FIG. 18, in the present embodiment, in regions other than the regions where the transducer cells 400 and the electrets 430 are disposed, the patterns formed by the same conductive layer as the upper electrode 420 (the solid lines in FIG. 18) and the patterns formed by the same conductive layer as the lower electrode 410 (the dashed lines in FIG. 18) are disposed so as not to overlap with each other.

That is, in the present embodiment, an upper electrode wiring 421 electrically connecting the plurality of upper electrodes 420 and the plurality of second conductive layers 424 is disposed in the row and column directions. On the other hand, a lower electrode wiring 411 electrically connecting the plurality of lower electrodes 410 and the plurality of first conductive layers 414 is disposed so as to form an angle of 45 degrees to the upper electrode wiring 421 when viewed from above.

Thus, by disposing the second conductive layers 424 and the first conductive layers 414 so as not to overlap with each other when viewed from above, generation of a parasitic capacitance is prevented in the wiring portions.

The transducer element 433 having the above-described configuration further includes the effects below in addition to the effects same as those in the fifth embodiment.

In the transducer element of the present embodiment, by disposing the electret 430 between the plurality of transducer cells 400, when viewing the transducer elements from the transmitting direction of ultrasonic waves, the area of the region not contributing to the transmission and reception of ultrasonic waves can be made smaller than that in the fifth embodiment. That is to say, utilization efficiency of the ultrasonic waves transmitting/receiving surface of the transducer element can be improved.

Therefore, the transducer element of the present embodiment is capable of providing a smaller-sized ultrasonic diagnostic apparatus which can transmit and receive ultrasonic waves with higher efficiency.

Note that the electrets 430 would suffice to retain an amount of charge sufficient to apply direct current voltage to the transducer cells 400 of the transducer element 433, and the electrets 430 do not have to be disposed in all the regions between the plurality of transducer cells 400, as shown in FIG. 18.

In addition, though the electrets are disposed dividedly in a plurality of regions in the above-described present embodiment, the electrets may be disposed in a single continuous shape as long as the electrets are disposed in a separated region different from the region where the transducer cells are formed.

Figure 20:
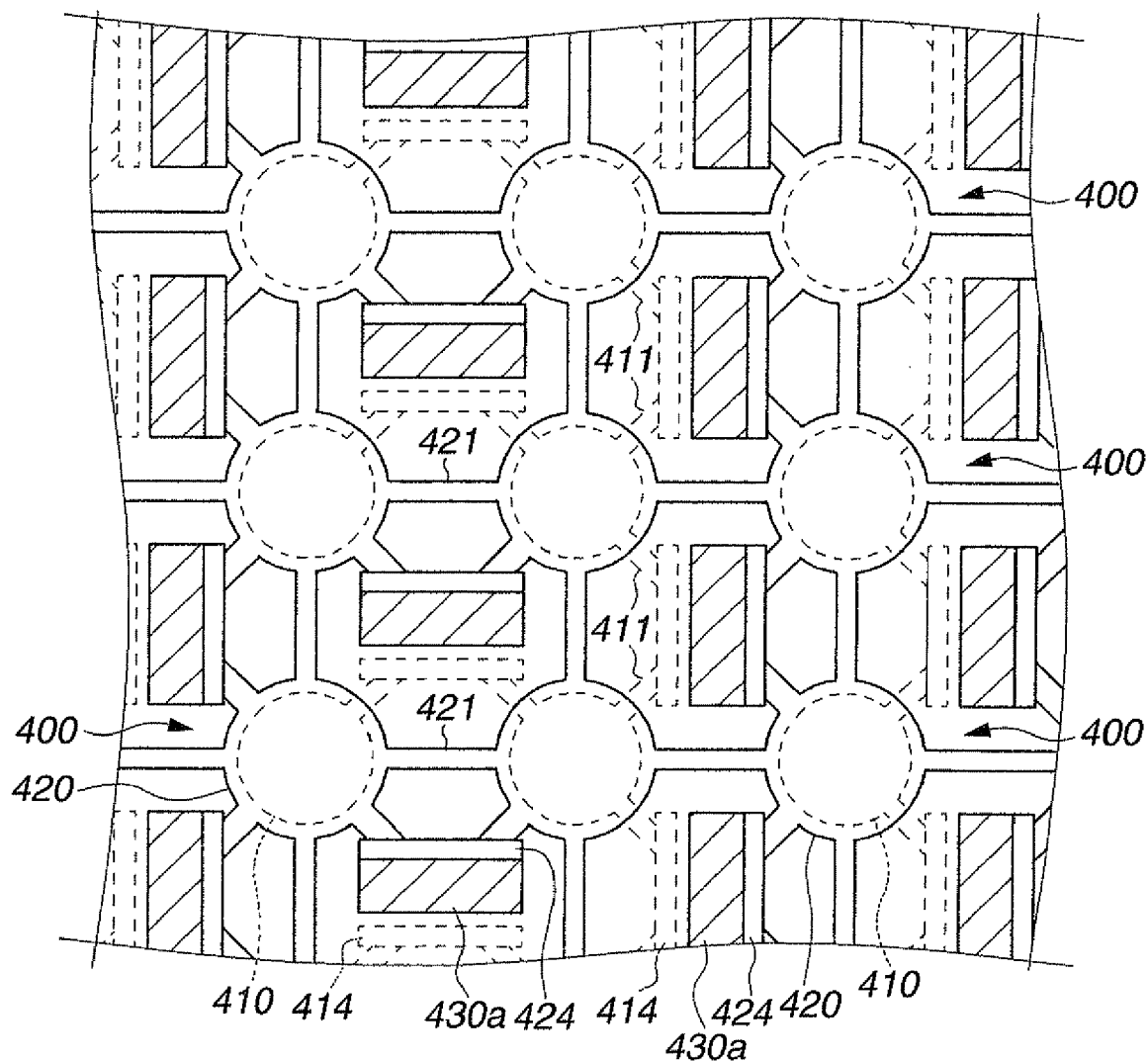
FIG. 20 is a top view of a transducer element according to a modified example of the seventh embodiment.

For example, as shown in FIG. 20, when focusing on the transducer cells 400 at four places aligned adjacently one another in two rows and columns, the electrets 430*a* may be disposed at positions at equal distance from all of the transducer cells 400 at the four places in the direction perpendicular to the transmitting direction of ultrasonic waves.

As the method of charging processing to be performed on the electrets according to the above-described first to seventh embodiments, the corona discharge method has been described. However, the method of charging processing is not limited to the corona discharge method, and may be an electron beam irradiation method, an ion implantation method, for example, or may be other methods that can form a fixed charge in the layers.

Eighth Embodiment

Hereinafter, the eighth embodiment of the present invention is described with reference to FIGS. 21 to 26.

Below, only the difference with the first embodiment is described. The same components as those in the first embodiment are attached with the same reference numerals, and the descriptions thereof are appropriately omitted.

Figure 21:
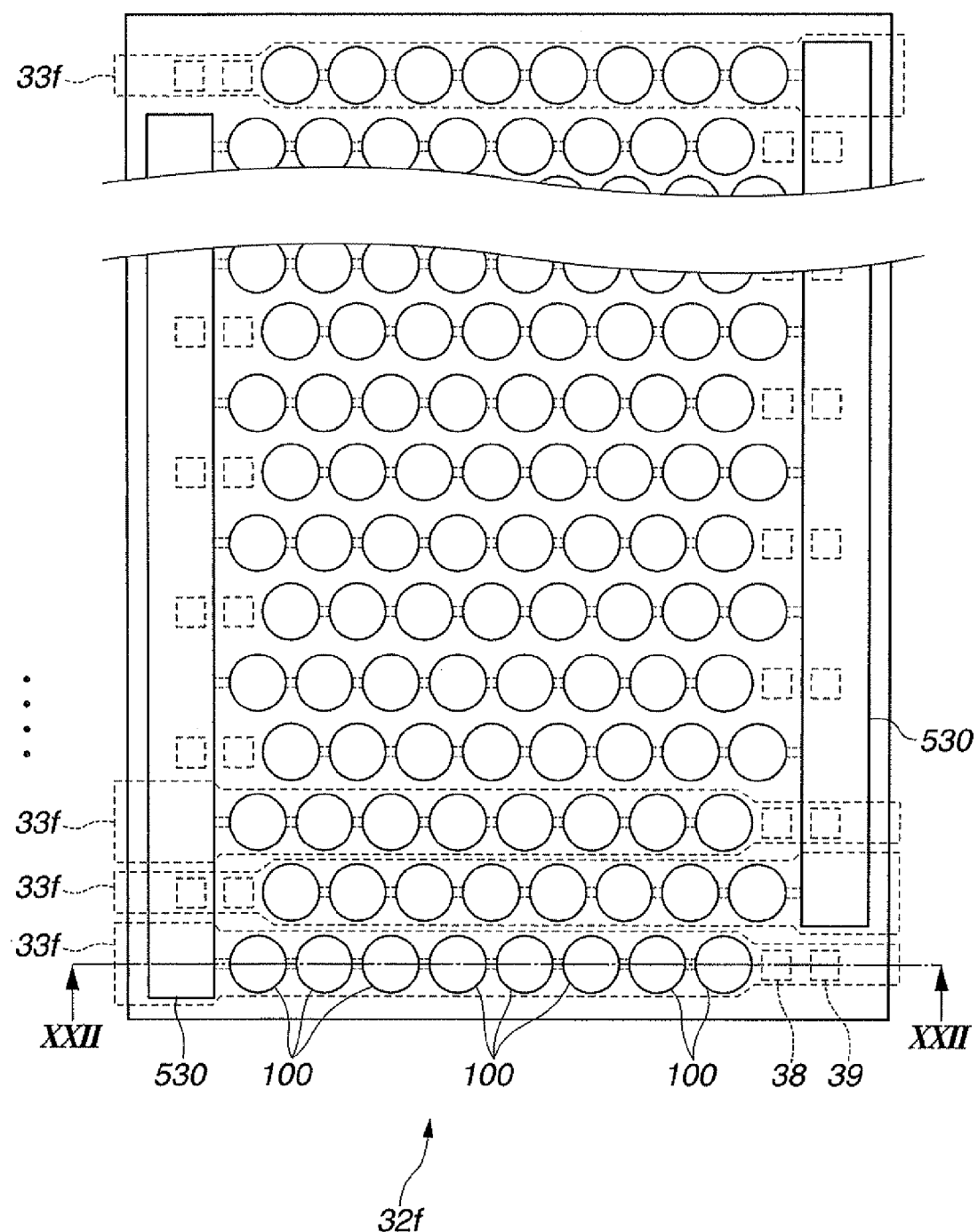
FIG. 21 is a top view of a transducer unit according to an eighth embodiment.
Figure 22:
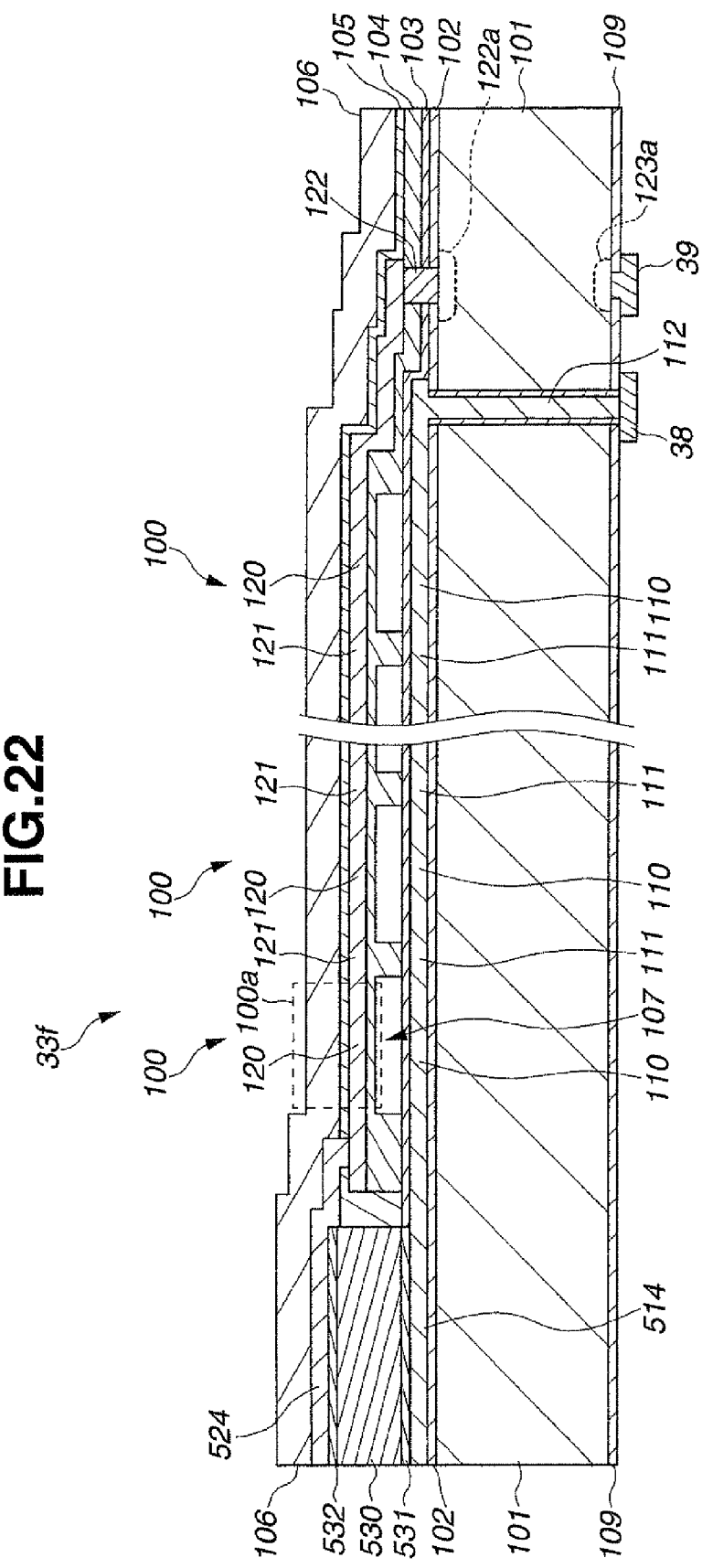
FIG. 22 is a cross-sectional view along the XXII-XXII line in FIG. 21.
Figure 23:
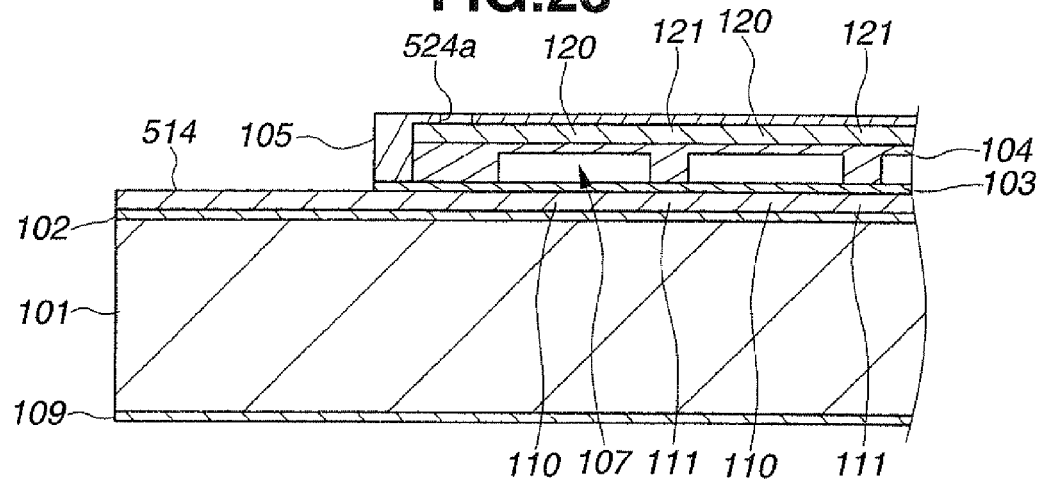
FIG. 23 is a view describing a manufacturing process of the transducer unit.
Figure 24:
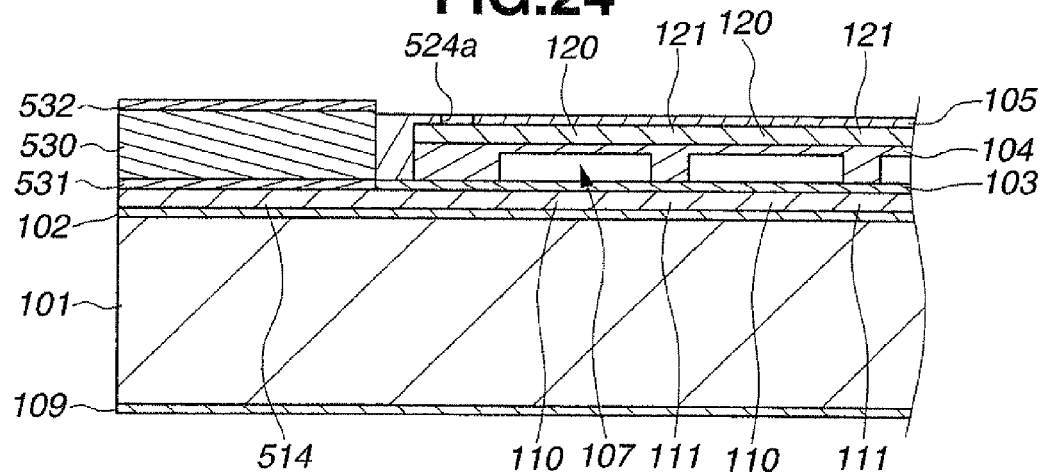
FIG. 24 is a view describing the manufacturing process of the transducer unit.
Figure 25:
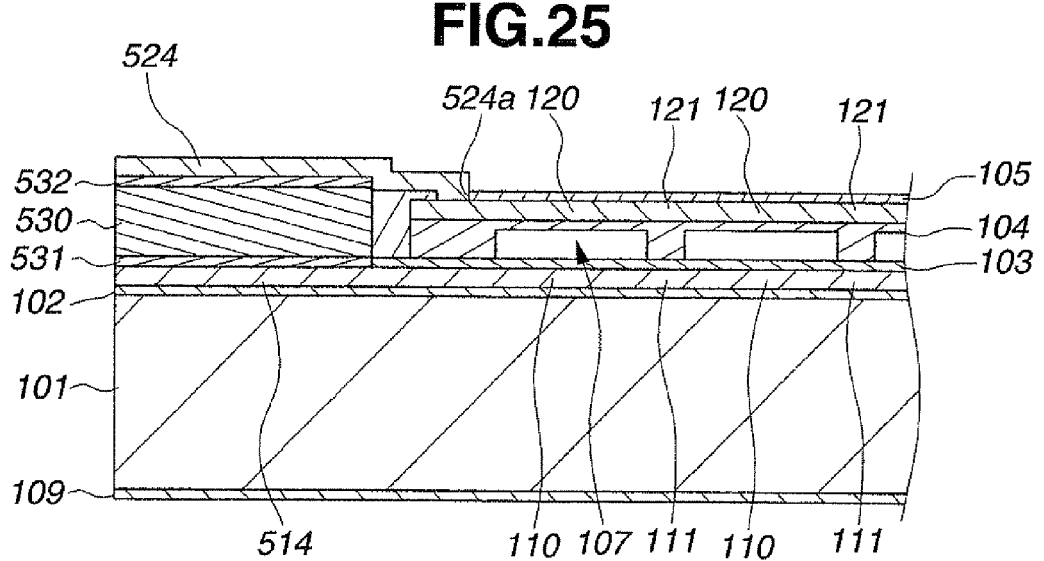
FIG. 25 is a view describing the manufacturing process of the transducer unit.

FIG. 21 is a top view of the transducer unit viewed from the transmitting/receiving side of ultrasonic waves. That is, in FIG. 21, ultrasonic waves are transmitted in the direction perpendicular to and away from the paper surface. FIG. 22 is a cross-sectional view along the XXII-XXII line in FIG. 21. FIGS. 23 to 25 are views describing the manufacturing method of the transducer unit.

As shown in FIG. 21, a transducer unit 32*f* of the present embodiment is configured of a plurality of transducer elements 33*f* aligned therein. In FIG. 21, an elongated region surrounded by a dashed line represents one piece of transducer element 33*f*.

The transducer element 33*f* is configured by including a plurality of transducer cells 100. In addition, the transducer element 33*f* is configured by including an electret 530 electrically connected to each of the plurality of transducer cells 100 configuring the transducer element 33*f*, the signal electrode pad 38, and the ground electrode pad 39.

The electret 530, which will be detailed later, retains a charge and supplies a DC bias voltage to the transducer cells 100. In addition, in the transducer unit 32*f* of the present embodiment, one piece of electret 530 is electrically connected to the plurality of transducer elements 33*f* to supply the DC bias voltage to the plurality of transducer cells 100 configuring each of the transducer elements 33*f*.

In the present embodiment, the transducer element 33*f* includes eight transducer cells 100 linearly aligned in the longitudinal direction of the elongated region, and the one piece of electret 530 disposed at one end of the elongated region and electrically connected in parallel to all of the eight transducer cells 100.

In the same transducer element 33*f*, the transducer cells 100 are all electrically connected in parallel each other, and inputted with a driving signal from the ultrasonic observation apparatus through the signal electrode pad 38, thereby simultaneously transmitting ultrasonic waves having the same phase.

Furthermore, the signal electrode pads 38 of all of the transducer elements 33*f* configuring the same transducer unit 32*f* are electrically connected to each other. Therefore, as described above, the one piece of transducer element 33*f* configures a minimum driving unit for transmitting and receiving ultrasonic waves.

As shown in FIG. 22, the transducer element 33*f* of the present embodiment is a capacitive ultrasonic transducer having a layer structure formed on the silicon substrate 101 composed of the low-resistance silicon semiconductors by the micromachining technology using a semiconductor process and the like, as in the first embodiment.

Since the configuration of the region where the transducer cells 100 are formed is the same as that in the first embodiment, the description thereof is omitted. Below, detailed description is made on the region of the ultrasonic transducer of the present embodiment, where the electret 530 is disposed.

In the present embodiment, the electret 530 as charge retention means is disposed and attached with an adhesive that cures at normal temperature on the end portion of the transducer element 33f having the elongated shape when viewed from above. The electret 530 has a function of permanently retaining a charge of positive or negative polarity.

The electret 530 of the present embodiment is made of an organic film, and particularly, formed by charging the fluorocarbon resin which is generally called as FEP, by the corona discharge. Note that the electret 530 may be configured of another organic film such as fluorocarbon resin other than FEP, polyimide, polypropylene, and the like.

In addition, specifically as shown in FIG. 22, the electret 530 of the present embodiment includes a lower conductive layer 531 and an upper conductive layer 532 formed on at least a part of both surfaces thereof in the thickness direction. The lower conductive layer 531 and the upper conductive layer 532 are metal films having a conductive property, such as copper, gold, and aluminum, and are disposed on the both surfaces of the electret 530 by known metal film-forming technology such as vapor deposition, CVD, adhesive bonding, ink-jet method, and the like.

In the transducer element 33f of the present embodiment, the lower conductive layer 531 formed on the lower side surface of the electret 530 is electrically connected to the lower electrodes 110 of the plurality of transducer cells 100 through a lower electrode wiring 514 (a first conductive layer) having a conductive property. On the other hand, the upper conductive layer 532 (a second conductive layer) formed on the upper side surface of the electret 530 is electrically connected to the upper electrodes 120 of the plurality of transducer cells 100 through an upper electrode wiring 524 having a conductive property. The upper electrode wiring 524 is a film having a conductive property formed by an existing low temperature film-forming technology.

That is, in the one transducer element 33f, the electret 530 is electrically connected to the lower electrodes 110 and the upper electrodes 120 of the plurality of transducer cells 100. Here, since the upper electrode 120 of the transducer cell 100 is grounded, the electret 530 applies a potential difference between the lower electrode 110 and the upper electrode 120 as the pair of electrodes of the transducer cell 100.

In addition, as in the transducer cells 100 part, the paraxylylene resin film 106 is formed above the electret 530 and the upper conductive layer 532 and the upper electrode wiring 524 which are disposed above the electret 530. Note that it is more preferable that the paraxylylene resin film 106 includes fluorine (F) having high chemical resistance.

A method of manufacturing the transducer unit 32f of the present embodiment having the above-described configuration is described below. Note that, in the following description, the method of manufacturing parts other than the region where the electret 530 is formed is a well-known method performed by the semiconductor process. Therefore, the description thereof is omitted or made simply.

First, as shown in FIG. 23, by the sacrificial layer etching as a known technology in the technical fields of the semiconductor process and the so-called MEMS, the lower electrode 110 and the upper electrode 120 as the pair of parallel plate electrodes configuring the transducer cell 100 and the cavity 107 interposed between the electrodes are formed on the low-resistance silicon substrate 101 including on both surfaces thereof the first insulating film 102 and the rear surface insulating film 109 which are the silicon oxide film.

Specifically, the conductive layer made of Mo is patterned to form the plurality of electrodes 110 and the lower electrode wiring 514 which is electrically connected to the plurality of lower electrodes 110 and extended to the end portion of the transducer element 33f. Next, the second insulating film 103 and the third insulating film 104 are formed on the plurality of lower electrodes 110, and the plurality of cavities 107 are further formed between the second insulating film 103 and the third insulating film 104 by the sacrificial layer etching.

Next, the conductive layer made of Al is patterned to form the upper electrodes 120 on positions respectively facing the plurality of lower electrodes 110 through the cavities 107. Next, the protective film 105 having electrical insulation is formed so as to cover over the upper electrodes 120.

Then, a via hole 524a penetrating the protective film 105 in the thickness direction and electrically connected to the upper electrodes 120 is formed on the end portion side of the transducer element 33f where the electret 530 is disposed.

In the state where the above processes are terminated, on the cell forming surface side of the silicon substrate 101, the lower electrode wiring 514 electrically connected to the lower electrodes 110 and the via hole 524a formed on the protective film 105 and electrically connected to the upper electrodes 120 are exposed upward, that is, in the transmitting direction of ultrasonic waves, on the end portion side of the region serving as the transducer element 33f, where the electret 530 is disposed. Here, the lower electrode wiring 514 and the via hole 524a are formed in different regions separated from each other in a state where the cell forming surface of the silicon 101 is viewed from above.

Next, as shown in FIG. 24, the electret 530, which has been formed in a process other than the process of forming the layer structure on the silicon substrate 101 by the above-described semiconductor process, is attached on the lower electrode wiring 514 with an adhesive that cures at normal temperature.

Here, the electret 530 is formed by charging the fluorocarbon resin called FEP by the corona discharge as described above, and includes the lower conductive layer 531 and the upper conductive layer 532 which are metal films formed on both surfaces thereof. Therefore, by attaching the electret 530 on the lower electrode wiring 514 by the adhesive, the lower electrode wiring 514 and the lower conductive layer 531 are electrically connected.

Note that the process of forming the lower conductive layer 531 and the upper conductive layer 532 on the electret 530 subjected to the charging processing is performed under the condition of a temperature at which the charge retained by the electret 530 is not lost. For example, in a case where the electret 530 is formed by performing the charging processing on the fluorocarbon resin called FEP as in the present embodiment, if the electret 530 is heated up to a temperature not less than 100 degrees Celsius, the retained charge amount decreases. Therefore, in the present embodiment, the process of forming the lower conductive layer 531 and the upper conductive layer 532 on the electret 530 is performed under the condition that the temperature of the electret 530 is not more than 100 degrees Celsius.

Similarly, the process of attaching the electret 530 on the lower electrode wiring 514 by the adhesive is also performed under the condition of a temperature at which the charge retained by the electret 530 is not lost. In the present embodiment, this process is performed under the condition that the temperature of the electret 530 is not more than 100 degrees Celsius.

In addition, the method of disposing the electret 530 on the lower electrode wiring 514 is not limited to the one using the adhesive, and may be any method in which the lower electrode wiring 514 and the lower conductive layer 531 are electrically connected and the process is performed under the condition of a temperature at which the charge retained by the electret 530 is not lost.

In the state where the above processed are terminated, on the cell forming surface side of the silicon substrate 101, the via hole 524a electrically connected to the upper electrodes 120 and the upper conductive layer 532 formed on the electret 530 are exposed upward, that is, in the transmitting direction of ultrasonic waves, on the end portion side of the region serving as the transducer element 33f, where the electret 530 is disposed.

Next, as shown in FIG. 25, the upper electrode wiring 524 which is a metal film having a conductive property is formed so as to electrically connect the via hole 524a formed on the protective film 105 and the upper conductive layer 532.

The upper electrode wiring 524 is formed by a known low temperature metal film-forming technology in the present embodiment. By this process, the upper electrodes 120 and the upper conductive layer 532 formed on the electret 530 are electrically connected.

Note that the method of electrically connecting the via hole 524a formed on the protective film 105 and the upper conductive layer 532 is not limited to the present embodiment, and may be any method in which the upper electrode wiring 524 and the upper conductive layer 532 are electrically connected and the process is performed under the condition of a temperature at which the charge retained by the electret 530 is not lost. For example, the present invention may have a configuration in which an electrode pad electrically connected to the via hole 524a and an electrode pad electrically connected to the upper conductive layer 532 are electrically connected by a low temperature wiring forming process such as wire bonding, wire welding, and the like. In addition, for example, the present invention may adopt the method of attaching a metal film by an adhesive or a configuration in which a conductive paste is used for drawing the wiring by the ink-jet method or dispense method.

After the above processes described with reference to FIGS. 23 to 25, by further forming the paraxylylene resin film 106 on the upper layer side by the low temperature process such as the spin coat method and the vapor deposition method, the transducer unit 32f of the present embodiment shown in FIGS. 21 and 22 is formed. Note that the paraxylylene resin film 106 may be formed after the transducer unit 32f is mounted on the FPC 35.

Below, description is made on the effects of the ultrasonic transducer and the ultrasonic diagnostic apparatus according to the present embodiment having the above-described configuration.

In the transducer unit 32f of the present embodiment, when viewed from the transmitting direction of ultrasonic waves, that is, the layer direction of the lower electrode 110 and the upper electrode 120 as the pair of electrodes of the transducer cell 100, the electret 530 is disposed in a region not overlapping with the transducer cell 100. Therefore, the transducer unit 32f of the present embodiment can be configured to be thinner than the conventional ultrasonic transducer in which the c-MUT and the electret are layered in the thickness direction, that is, the transmitting direction of ultrasonic waves.

Incidentally, it is preferable that the thickness of the electret 530 is several micrometers to several tens of micrometers to allow the electret to have a high-density charge and a sufficient resistance to deterioration. On the other hand, in order to obtain in an ordinary c-MUT a capacitance between the electrodes enough to realize a sufficient sound pressure of ultrasonic waves and sensitivity to ultrasonic waves, the distance between the electrodes is preferably not more than 1 micrometer. That is, in the conventional c-MUT including the electrets disposed between the electrodes, the distance between the electrodes enough to obtain a necessary capacitance can not be ensured, and as a result, it has been impossible to transmit and receive ultrasonic waves at sufficient sound pressure and sensitivity.

On the other hand, the transducer unit 32f of the present embodiment can independently set the thickness of the electret 530 and the distance (gap) between the lower electrode 110 and the upper electrode 120. That is, the present embodiment improves the degree of freedom in the design of the transducer unit 32f, thereby, e.g., allowing to make the distance between the lower electrode 110 and the upper electrode 120 smaller than that in the conventional transducer unit to increase the capacitance between the electrodes and improve the sound pressure of the transmitted ultrasonic wave and the sensitivity to the received ultrasonic waves, and allowing the electret 530 to have a thickness to permit permanent and stable charge retention. In addition, in this state, the transducer unit 32f can be configured to be thinner than conventional ones.

Therefore, according to the present embodiment, the transducer unit 32f is thinner in the transmitting direction of ultrasonic waves and has a higher sound pressure of the transmitted ultrasonic waves and a higher sensitivity to the received ultrasonic waves than conventional transducer units, and the electret 530 has performance more stable than conventional transducer units. Therefore, the performance of the transducer unit can be maintained over a longer period of time.

In other words, the transducer unit 32f of the present embodiment can realize an ultrasonic transducer with higher efficiency than conventional ones, and in a case of exerting predetermined sound pressure of the transmitted ultrasonic waves and sensitivity to the received ultrasonic waves, the transducer unit 32f can realize an ultrasonic transducer which maintains the initial performance over a long period of time, and which is thinner and drivable at a lower voltage than the conventional ones.

Incidentally, in the case of the conventional ultrasonic transducer in which the c-MUT and the electret are layered in the thickness direction, that is, the transmitting direction of ultrasonic waves, there is a problem that the performance of the electret is deteriorated by the influence of components, humidity, and temperature of the atmosphere in the manufacturing process performed after the charging processing on the electret.

For example, in the conventional ultrasonic transducer configured by layering the c-MUT and the electret, after forming the electret, it is required to further form the layer structure such as of a silicon oxide film using the semiconductor process. That is, the electret is heated up to several hundred degrees Celsius in a later semiconductor process. Therefore, in the conventional ultrasonic transducer, it is impossible to use as an electret an organic film such as FEP whose retaining charge disappears at approximately 100 degrees Celsius.

In order to prevent the disappearance of the charge retained by the electret, the conventional electret is configured of an inorganic film made of, for example, a silicon compound capable of retaining a charge at a higher temperature in the conventional ultrasonic transducer.

However, the electret configured of the inorganic film made of the silicon compound and the like suffers from a problem of a lower charge retention capacity after subjected to the charging processing and difficulty to permanently and stably retain the charge, compared with an electret configured of an organic film. That is, in a conventional ultrasonic transducer configured by including an electret made of an inorganic film, characteristics such as the sound pressure of the transmitted ultrasonic waves and the sensitivity to the received ultrasonic waves change over time.

On the other hand, in the present embodiment, the electret 530 is formed in a process different from the semiconductor process of forming the transducer cells 100, in which the electret 530 is attached on the transducer unit 32f after all the layer structures configuring the transducer cells 100 have been formed. In addition, the electret 530 is attached on the transducer unit 32f under the condition of a temperature at which the retaining charge is not lost, and also electrically connected to the lower electrodes 110 and the upper electrodes 120 of the transducer cells 100. In other words, in the present embodiment, after the charging processing, the electret 530 made of the organic film is not heated to a temperature at which the retaining charge decreases or disappears.

Therefore, unlike the conventional ultrasonic transducer including the electret made of the inorganic film, the transducer unit 32f as the ultrasonic transducer of the present embodiment is capable of using an electret made of an organic film which can stably retain the charge over a longer period of time. The transducer unit 32f is thus enable to maintain characteristics constant over a longer period of time.

Note that, in order to shield the exogenous noise and improve the S/N ratio, ultrasonic diagnostic apparatuses including an ultrasonic transducer in some cases to cover the ultrasonic transducer with a shield layer as a conductive layer grounded electrically independently of the ultrasonic transducer.

In the case of applying the shield layer to the above-described embodiment, for example, if the process of covering the transducer cells 100 with the shield layer is performed at a temperature at which the charge amount retained by the electret 530 decreases, the process of disposing the electret 530 on the lower electrode wiring 514 is performed after the shield layer has been formed on the transducer cells 100. However, the above is not the case, if the process of covering the transducer cells 100 with the shield layer is performed at a temperature lower than the temperature at which the charge amount retained by the electret 530 decreases, for example.

In addition, though in the above-described embodiment, the electret 530 is electrically connected to the silicon substrate 101 as the ground potential through the upper conductive layer 532, the upper electrode wiring 524, and the upper electrode 120, the upper conductive layer 532 may be, for example, directly connected to the electrode pad formed on the silicon substrate 101 by wire bonding and the like.

Ninth Embodiment

Figure 26:
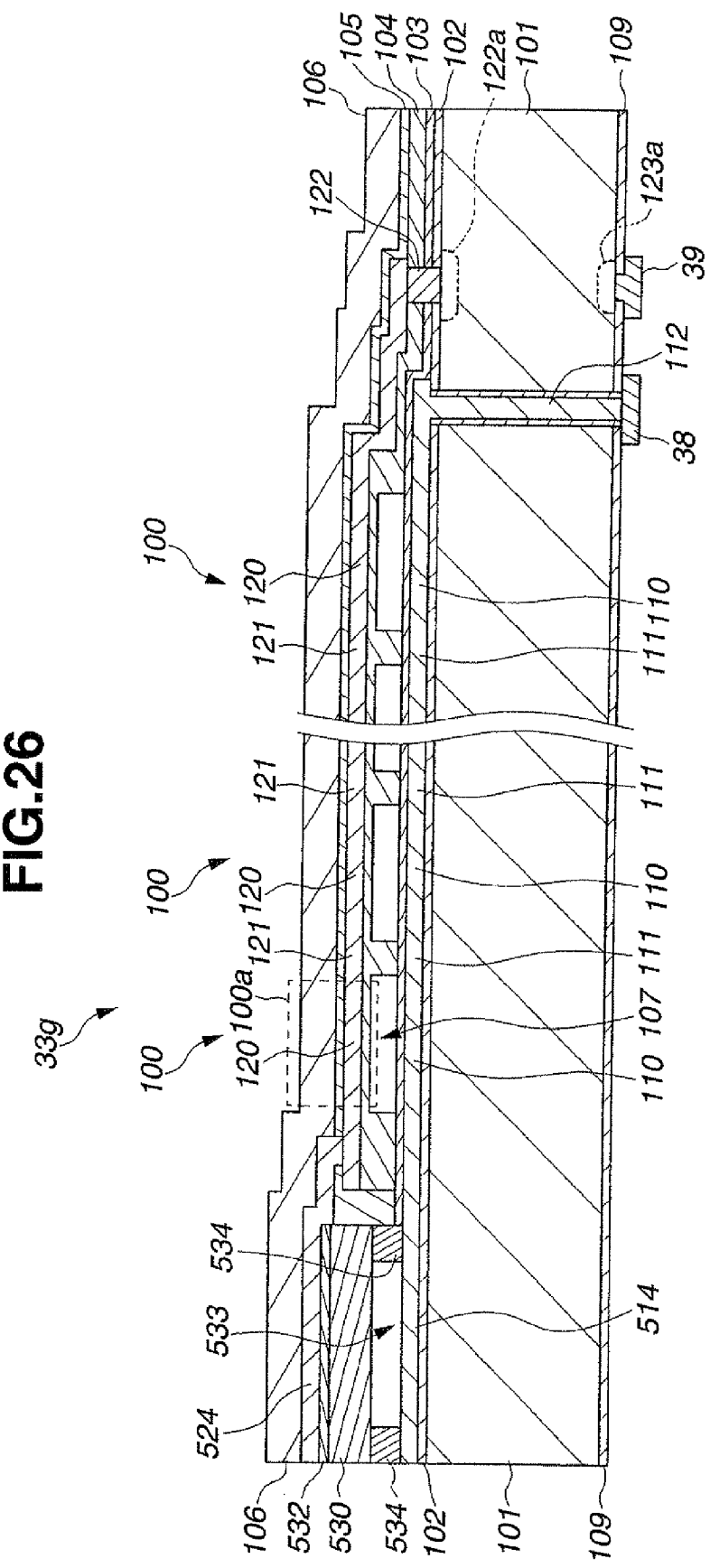
FIG. 26 is a cross-sectional view of a transducer element according to a ninth embodiment.

Hereinafter, the ninth embodiment of the present invention is described with reference to FIG. 26. FIG. 26 is a cross-sectional view of the transducer element according to the ninth embodiment.

The ninth embodiment is different from the eighth embodiment only in the configuration of the region where the electret is disposed. Therefore, only the different point is described. The same components as those in the eighth embodiment are attached with the same reference numerals, and the descriptions thereof are appropriately omitted.

In the transducer unit of the present embodiment, an air gap portion 533 is interposed between the lower electrode wiring 514 formed in an extended manner to one end of a transducer element 33g and the electret 530 disposed above the lower electrode wiring 514.

Specifically, spacers 534 are formed on the lower electrode wiring 514 to separate the electret 530 from the lower electrode wiring 514 by a predetermined interval, and the electret 530 is attached on the spacers 534.

For example, as in the above-described eighth embodiment, when the lower conductive layer 531 and the upper conductive layer 532, which are conductive layers, are disposed directly on the surfaces of the electret 530, the charging state of the electret 530 is in some cases neutralized by the charge trapped in a deficiency in the vicinity of an interface between the electret 530 and the conductive layers, which as a result renders the electret 530 into the same state as that in which the retaining charge amount thereof has decreased.

However, in the transducer element of the present embodiment, the air gap portion 533 is provided between the electret 530 and the lower electrode wiring 514 electrically connected to the lower electrodes 110 to which a signal voltage is supplied, which can eliminate influences caused by the charge trapped in the deficiency in the vicinity of the interfaces of the conductive layers.

That is, according to the present embodiment, the charge retained by the electret 530 can be more efficiently utilized as direct current voltage components to be supplied between the lower electrodes 110 and the upper electrode 120 of the transducer cells 100, thereby enabling to configure a transducer element having a higher sound pressure of the transmitted ultrasonic waves and a higher sensitivity to the received ultrasonic waves.

Tenth Embodiment

Figure 27:
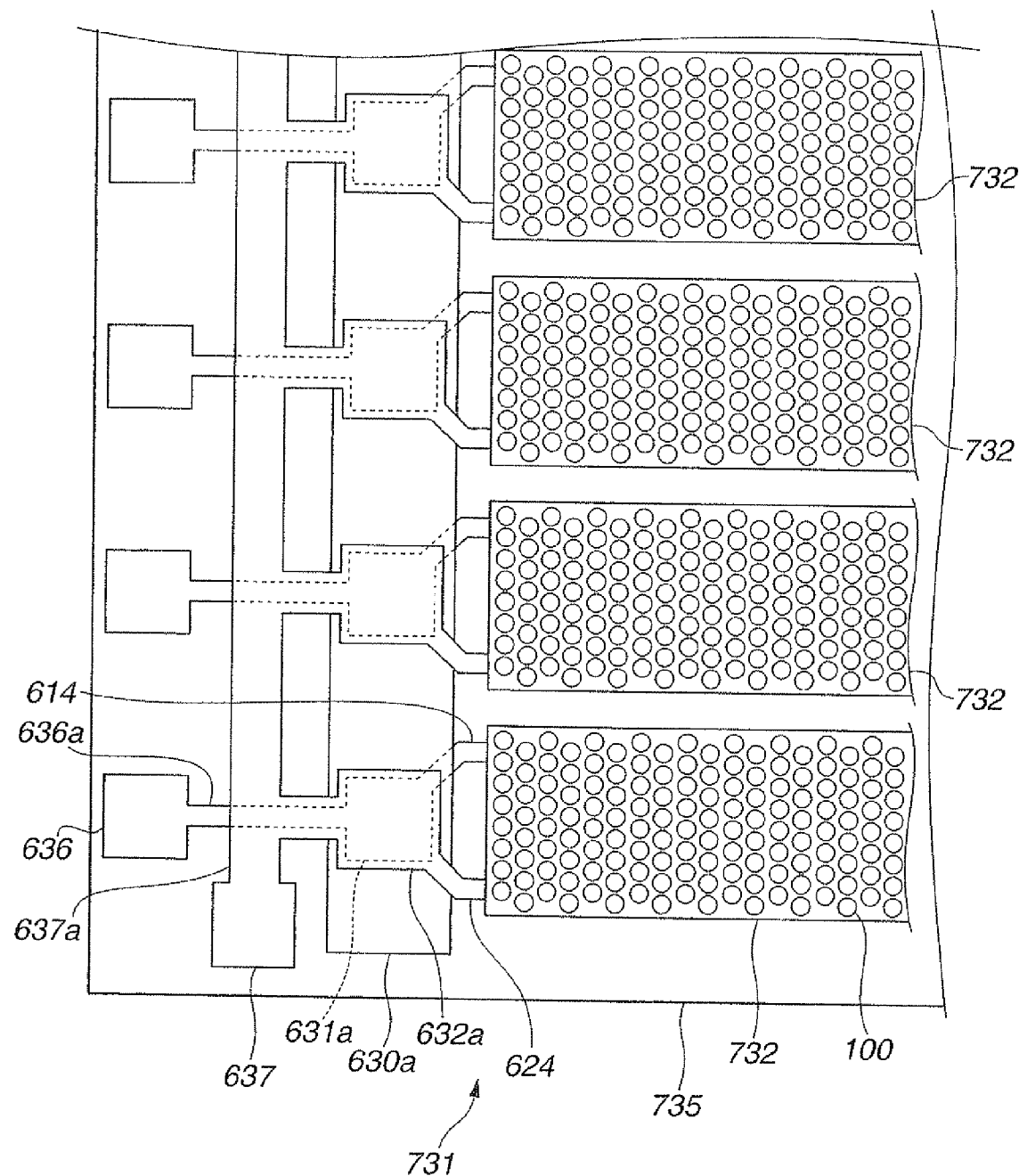
FIG. 27 is a top view of a transducer array according to a tenth embodiment.

Hereinafter, the tenth embodiment of the present invention is described with reference to FIG. 27. FIG. 27 is a top view of the ultrasonic transducer array 731 of the present embodiment.

The above-described eighth embodiment is configured such that one electret is electrically connected to the plurality of transducer elements and to supply the direct current voltage components to each of the plurality of transducer cells configuring the transducer element. On the other hand, the present embodiment is configured such that one electret is electrically connected to a plurality of transducer units.

As shown in FIG. 27, an ultrasonic transducer array 731 as an ultrasonic transducer of the present embodiment is configured such that a plurality of transducer units 732 composed of a plurality of transducer cells 100 are mounted on a mounting surface of an FPC 735.

When focusing on the one transducer unit 732, on the FPC 735 are formed a lower electrode wiring 614, a lower electrode pad 631a, a signal electrode wiring 636a and a signal electrode pad 636, all of which are electrically connected to the lower electrodes 110 of all of the transducer cells 100 configuring the one transducer unit 732.

Note that, among the lower electrode wiring 614, the lower electrode pad 631a, the signal electrode wiring 636a and the signal electrode pad 636 which are electrically connected to the lower electrodes 110, the lower electrode wiring 614 and the signal electrode wiring 636a are formed as conductive patterns on a lower layer side of the FPC 735 and are insulated from the surface of the FPC 735. On the other hand, the lower electrode pad 631a and the signal electrode pad 636 are conductive patterns formed so as to be exposed on the uppermost surface of the mounting surface side of the FPC 735.

In addition, one electret 630a is attached on and electrically connected to the plurality of lower electrode pads 631a provided corresponding to the plurality of transducer units 732. Furthermore, on the surface of the electret 630a, which is opposite to the surface attached to the lower electrode pad 631a, that is, the surface on the opposite side of the FPC 735, the upper conductive layers 632a are formed corresponding to the positions of the lower electrode pads 631a.

Each of the upper conductive layers 632a is electrically connected to the upper electrodes 120 of all the transducer cells 100 configuring the one transducer unit 732, through the upper electrode wiring 624 formed by the wire bonding and the like.

Moreover, all of the plurality of upper conductive layers 632a formed on the electret 630a are electrically connected to a common ground electrode pad 637 formed so as to be exposed on the uppermost surface on the mounting surface side of the FPC 735, through a ground electrode wiring 637a. That is, in the transducer array 631 of the present embodiment, the upper electrodes 120 of the transducer cells 100 of all of the transducer units 732 are electrically connected to the common ground electrode pad 637.

In the ultrasonic transducer array 731 having the above-described configuration, the plurality of transducer units 732 are electrically connected to the one electret 630a, and the one transducer unit 732 configures the minimum driving unit for transmitting and receiving ultrasonic waves. In addition, the electret 630a applies a potential difference between the lower electrodes 110 and the upper electrodes 120 of the transducer cells 100 configuring the transducer unit 732.

According to the above-described present embodiment, it is possible to form the chip-shaped transducer units 732 and the electret 630a applying a potential difference to the transducer cells 100 of the transducer units 732, in different regions not overlapping with each other on the FPC 735.

That is, the present embodiment can further reduce the entire thickness of the transducer array, compared with the eighth embodiment in which the electret is disposed for each transducer unit.

Furthermore, compared with the eighth embodiment, the size of the electret can be increased, which can facilitate the processes of forming and attaching the electret.

Eleventh Embodiment

Figure 28:
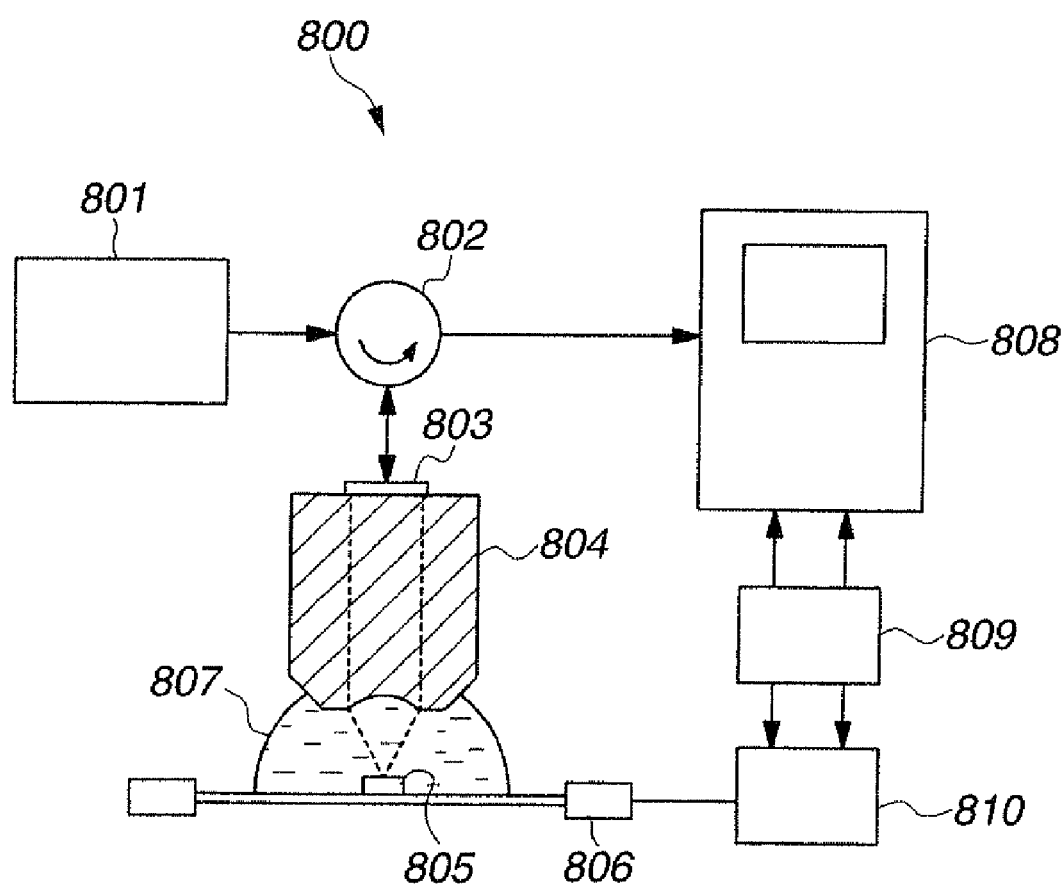
FIG. 28 is an illustration diagram showing a schematic configuration of an ultrasonic microscope.

Hereinafter, the eleventh embodiment of the present invention is described with reference to FIG. 28. The eleventh embodiment applies the ultrasonic transducer according to the above-described present invention to an ultrasonic microscope. FIG. 28 is a view describing the configuration of the ultrasonic microscope of the present embodiment.

An ultrasonic microscope 800 applies a high-frequency signal generated by a high-frequency oscillator 801 to an ultrasonic transducer 803 according to the present invention through a circulator 802 and converts the high-frequency signal into ultrasonic waves. The ultrasonic waves are converged by an acoustic lens 804, and a sample 805 is placed on the converging point of the acoustic lens 804. The sample 805 is held by a sample holder 806, and a coupler 807 such as water is filled between the sample 805 and a lens surface of the acoustic lens 804. Reflected waves from the sample 805 are received by the transducer 803 through the acoustic lens 804 to be converted into an electrical reflected signal. An electric signal corresponding to the received ultrasonic waves outputted from the ultrasonic transducer 803 is inputted to a display device 808 through the circulator 802. The sample holder 806 is driven in directions of two axes X, Y in a horizontal surface by a scan device 810 controlled by a scan circuit 809.

The ultrasonic microscope 800 thus configured can quantify the elastic property of the sample 805 and evaluate the structure of a thin film by irradiating ultrasonic waves to the sample 805 and evaluating the acoustic property of the sample 805.

Note that the present invention is not limited to the above-mentioned embodiments, but may be properly changed without departing from the gist and spirit of the present invention readable from the appended claims and the entire specification, and an ultrasonic transducer, a method of manufacturing the ultrasonic transducer, a ultrasonic diagnostic apparatus, and an ultrasonic microscope with such changes are also included in the technical field of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic transducer comprising:
   a transducer cell including: a first electrode; a vibration membrane disposed on the first electrode, separated by an air gap portion; and a second electrode supported by the vibration membrane;
   a first conductive layer electrically connected to the first electrode;
   a second conductive layer disposed facing the first conductive layer and electrically connected to the second electrode;
   an electret for retaining a charge and applying a predetermined potential difference between the first electrode and the second electrode, the electret being disposed in a region between the first conductive layer and the second conductive layer, where the electret do not overlap with the transducer cell when viewed from a transmitting direction of ultrasonic waves generated by vibration of the vibration membrane.

2. The ultrasonic transducer according to claim 1, wherein the electret has a region exposed in the transmitting direction of ultrasonic waves, relative to at least one of the first conductive layer and the second conductive layer.

3. The ultrasonic transducer according to claim 2, wherein the second conductive layer is disposed above the first conductive layer, and a through hole is formed in a region on the second conductive layer, which overlaps with the electret when viewed from the transmitting direction of ultrasonic waves.

4. The ultrasonic transducer according to claim 2, wherein the first conductive layer and the second conductive layer are disposed facing each other in a direction perpendicular to a direction in which the first electrode and the second electrode face each other.

5. The ultrasonic transducer according to claim 2, wherein the electret is disposed on a third conductive layer having the same potential as that of the second electrode, and
   wherein the first conductive layer is disposed above the electret, and a through hole is formed in a region on the first conductive layer, which overlaps with the electret when viewed from the transmitting direction of ultrasonic waves.

6. The ultrasonic transducer according to claim 1, further comprising a protective film for covering a surface on a side of the transmitting direction of ultrasonic waves, wherein a region on the protective film, which overlaps with the electret, is projected in the transmitting direction of ultrasonic waves more than a region on the protective film, which overlaps with the transducer cell.

7. The ultrasonic transducer according to claim 1, further comprising a protective film for covering a surface on a side of the transmitting direction of ultrasonic waves, wherein a surface of the protective film on the side of the transmitting direction of ultrasonic waves has a plane shape.

8. The ultrasonic transducer according to claim 1, wherein an insulating layer is interposed between the electret and the first conductive layer, or between the electret and the second conductive layer.

9. The ultrasonic transducer according to claim 8, wherein a distance between the first conductive layer and the second conductive layer separated by the insulating layer is larger than a distance between the first electrode and the second electrode separated by the air gap portion in the transducer cell.

10. The ultrasonic transducer according to claim 1, wherein the electret is attached on the first conductive layer.

11. The ultrasonic transducer according to claim 10, wherein the electret is attached over a plurality of the first conductive layers.

12. The ultrasonic transducer according to claim 10, wherein an air gap portion is interposed between the electret and the first conductive layer or between the electret and the second conductive layer.

13. An ultrasonic diagnostic apparatus comprising the ultrasonic transducer according to claim 1.

14. The ultrasonic diagnostic apparatus according to claim 13, wherein the ultrasonic diagnostic apparatus is an ultrasonic endoscope including the ultrasonic transducer disposed in an insertion portion to be introduced in a living body.

15. An ultrasonic microscope comprising the ultrasonic transducer according to claim 1.

* * * * *